United States Patent [19]

Loh

[11] Patent Number: 4,554,011

[45] Date of Patent: Nov. 19, 1985

[54] HERBICIDAL 2S-(2β,4β,5β)-5-ARYLMETHOXY-4-SUBSTITUTED 2-ALKYL-1,3-DIOXANE DERIVATIVES

[75] Inventor: William Loh, Petaluma, Calif.

[73] Assignee: Chevron Research Company, San Francisco, Calif.

[21] Appl. No.: 645,451

[22] Filed: Aug. 24, 1984

[51] Int. Cl.[4] ............... A01N 43/00; C07D 401/00; C07D 319/06
[52] U.S. Cl. ................................. 71/88; 546/268; 549/60; 549/372
[58] Field of Search ............ 549/372, 60; 71/88; 546/268

[56] References Cited

U.S. PATENT DOCUMENTS

| | | | |
|---|---|---|---|
| 3,024,249 | 3/1962 | Wöllner | 549/372 |
| 3,753,678 | 8/1973 | Young | 71/88 |
| 3,862,959 | 1/1975 | Kirby et al. | 260/340.9 |
| 3,887,472 | 6/1975 | Kirby et al. | 260/340 |
| 3,981,860 | 9/1976 | Szkrybalo | 536/4 |
| 3,986,860 | 10/1976 | Kirby et al. | 71/88 |
| 4,059,594 | 11/1977 | Konz | 260/340 |
| 4,077,982 | 3/1978 | Young | 260/340 |
| 4,207,088 | 6/1980 | Konz | 549/372 |
| 4,376,860 | 3/1983 | Booher | 546/268 |

FOREIGN PATENT DOCUMENTS

| | | |
|---|---|---|
| 816425 | 12/1974 | Belgium . |
| 2243685 | 9/1972 | Fed. Rep. of Germany . |
| 2247030 | 9/1972 | Fed. Rep. of Germany . |
| 2258013 | 11/1972 | Fed. Rep. of Germany . |
| 2326586 | 5/1973 | Fed. Rep. of Germany . |
| 1148247 | 4/1969 | United Kingdom ............ 549/372 |

*Primary Examiner*—Ethel G. Love
*Attorney, Agent, or Firm*—J. A. Buchanan, Jr.; T. G. DeJonghe; L. S. Squires

[57] ABSTRACT

2S-(2β,4β,5β)-5-Arylmethoxy-4-substituted 2-alkyl-1,3-dioxane and derivatives thereof. The compounds are especially useful as herbicides.

40 Claims, No Drawings

HERBICIDAL 2S-(2β,4β,5β)-5-ARYLMETHOXY-4-SUBSTITUTED 2-ALKYL-1,3-DIOXANE DERIVATIVES

BACKGROUND OF THE INVENTION

This invention relates to herbicidal 2S-(2β,4β,5β)-5-Arylmethoxy-4-Substituted 2-Alkyl-1,3-Dioxane derivatives and to the use of such compounds as herbicides and plant growth regulators.

Herbicidal 1,3-dioxanes having certain substituents other than hydrogen at the 2, 4, 5, and/or 6 position are described in U.S. Pat. Nos. 4,207,088 and 4,035,178 and published German Patent Application DE No. 2739067. More particularly U.S. Pat. No. 4,207,088 describes certain 1,3-dioxanes substituted at the 4-position with an alkyl group optionally substituted with halo, cyano or alkoxy. A variety of 1,3-dioxane herbicides is also described in U.S. Pat. Nos. 3,753,678; 3,887,472; 3,862,959; 3,981,860; 3,986,860; 4,059,594; and 4,077,982; German Patent Applications Nos. 2,243,685; 2,247,030; 2,258,013 and 2,326,586 and Belgian Pat. No. 816,425.

SUMMARY OF THE INVENTION

The present invention provides compounds having pre-emergence herbicidal activity and generaly also having post-emergence herbicidal activity. The compounds have especially good pre-emergence activity against grassy weeds. I have found that in the dioxane compounds the stereo configuration as well as the size and type of substituents greatly influences herbicidal activity and in some instances is critical thereto.

At lower application rates the compounds can be used as plant growth regulators.

The compounds of the present invention can be represented by the following formula:

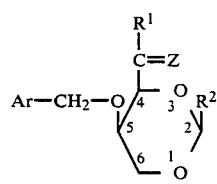
(I)

wherein
$R^1$ is methyl, ethyl, n-propyl or n-butyl;
$R^2$ is lower alkyl having 1 through 6 carbon atoms;
Ar is phenyl, thienyl, pyridyl or substituted phenyl having 1 or 2 substituents independently selected from the group of lower alkyl having 1 through 6 carbon atoms; lower alkoxy having 1 through 6 carbon atoms; halo; and haloalkyl having 1 or 2 carbon atoms and 1 through 4 of the same or different halo atoms; and
Z is oxo or the group

wherein the waxy bond line indicates that the carbon to which the $OR^3$ group is attached to can be R or S oriented, and $R^3$ is hydrogen, lower alkanoyl having 2 through 6 carbon atoms, benzoyl, phenoxyacetyl or substituted phenoxyacetyl having one or two substituents on the phenyl ring independently selected from the group of fluoro, chloro, bromo, iodo or trifluoromethyl;

The compounds of Formula I of the invention have the stereo configuration 2-S-(2β,4β,5β).

The compounds have at least one asymmetric carbon atom and exist as enantiomers and/or diastereomers. For example, as noted above, the wavy bond line, with respect to $OR^3$, indicates diastereomers. Also, the C-2 carbon is chiral and hence these compounds exist in enantiomeric forms. The above formula is intended to encompass the respective individual isomers as well as mixtures thereof, and the respective isomers as well as mixtures thereof are encompassed within the invention.

It is also important to note that the compounds of the present invention are optical isomers which are designated [2S-(2β,4β,(SR),5β)] or [2R-(2β,4β,(SR),5β)]. This is important because the isomers designated [2R-(2β,4β,,5β)] exhibit very weak or no herbicidal activity.

In a further aspect the invention provides a herbicidal composition comprising a compatible carrier and a herbicidally effective amount of the compound(s) of the invention, or mixtures thereof.

The present invention also provides a method for preventing or controlling the growth of unwanted vegetation, which comprises treating the growth medium and/or the foliage of such vegetation with a herbicidally effective amount of the compound(s) of the invention or mixtures thereof.

In another aspect, the present invention provides a plant growth regulating composition comprising a compatible carrier and a plant growth regulating amount of the compound(s) of the invention, or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of the invention, or mixtures thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

The compounds of the present invention can also be represented by the following subgeneric formulas:

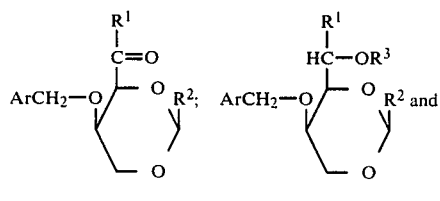

(Ia)                (Ib)

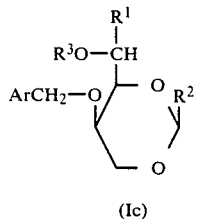

(Ic)

wherein Ar, $R^1$, $R^2$ and $R^3$ are as defined hereinabove.

Illustrations of typical compounds of the present invention can be had by reference to Examples 7-9, 14, 15 and 21-24 set forth hereinbelow on Pages 24-29, 31-36 and 39-44. In terms of herbicidal activity and substituents, the preferred compounds are those wherein Ar is 2-halophenyl, 2-alkylphenyl or 2-trifluoromethylphenyl and especially 2-chlorophenyl, 2-fluorophenyl and 2-methylphenyl. Preferably, $R^1$ is methyl or ethyl, most preferably, methyl. Preferably, $R^2$ is methyl, ethyl, propyl or isopropyl and more preferably ethyl or propyl. Preferably, Z is oxo or the group

wherein $R^3$ is hydrogen, acetyl, propionyl, butyryl, benzoyl, or 2,4-dichlorophenoxyacetyl and most preferably $R^3$ is benzoyl or acetyl. Most preferably the compounds contain a combination of two or more preferred substituents.

In terms of ease of synthesis, the compounds are preferably prepared either as a mixture of isomers 2S-[2β,4β(S),5β], 2R-[2β-4β(R),5β], 2S-[2β,4β(R),5β], and 2R-[2β-4β(S),5β] or as the pure isomer (i.e., Formula Ib 2S-[b 2β,4β(S),5β]). The synthesis of the compounds of Formula Ib,2S-[2β,4β(R),5β], are preferred over their isomer (i.e., Formula IC, 2S-[2β,4β(R),5β] because of the ease of separation of certain of the corresponding diastereomeric intermediates in the general synthesis. The synthesis of the compounds of Formula Ia from Ib and Ic where $R^3=H$ does not require the separation of isomers of Ib and Ic where $R^3=H$ as both isomers are converted to the same Ia.

The compounds of Formula (I) can be conveniently prepared by the following schematically represented process:

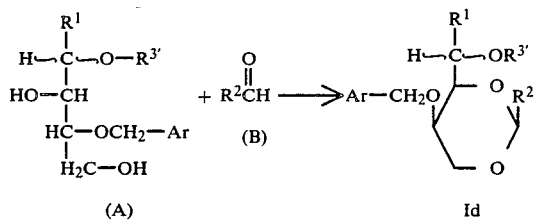

wherein Ar, $R^1$, $R^2$, and the wavy bond lines are as defined herinabove and $R^{3'}$ is as defined for $R^3$ but is not hydrogen. Preferably, in terms of ease of synthesis, $R^{3'}$ is benzoyl.

This process can be conveniently effected by contacting Compound (A) with an aldehyde having the desired $R^2$ group (i.e., compound B) preferably in the presence of a strong acid and preferably in an inert organic solvent.

The process can be conducted using a mixture of isomers or the optically active D-xylo or D-lyxo isomer as depicted by the Fischer projection formula for compound (A), in which case the product will be the corresponding optically active isomer.

Typically, this process is conducted under substantially anhydrous conditions at temperatures in the range of about from $-25°$ to $100°$ C., preferably about from $0°$ to $25°$ C., for about from 1 to 48 hours, preferably about from 2 to 12 hours, using about from 1 to 10, preferably 1 to 2 moles of B per mole of Compound (A). Suitable acids which can be used include, for example, p-toluenesulfonic acid, camphorsulfonic acid, hydrogen chloride, sulfuric acid, zinc chloride, dry cation-exchange resin (H+ form), and the like. Suitable inert organic solvents which can be used include, for example, toluene, benzene, xylene, ethyl ether, methylene chloride, p-dioxane, N,N-dimethylformamide, and the like, and compatible mixtures thereof.

Best results are obtained using toluene, or xylene.

The starting materials of Formula (A) can be prepared by the following schematically represented process:

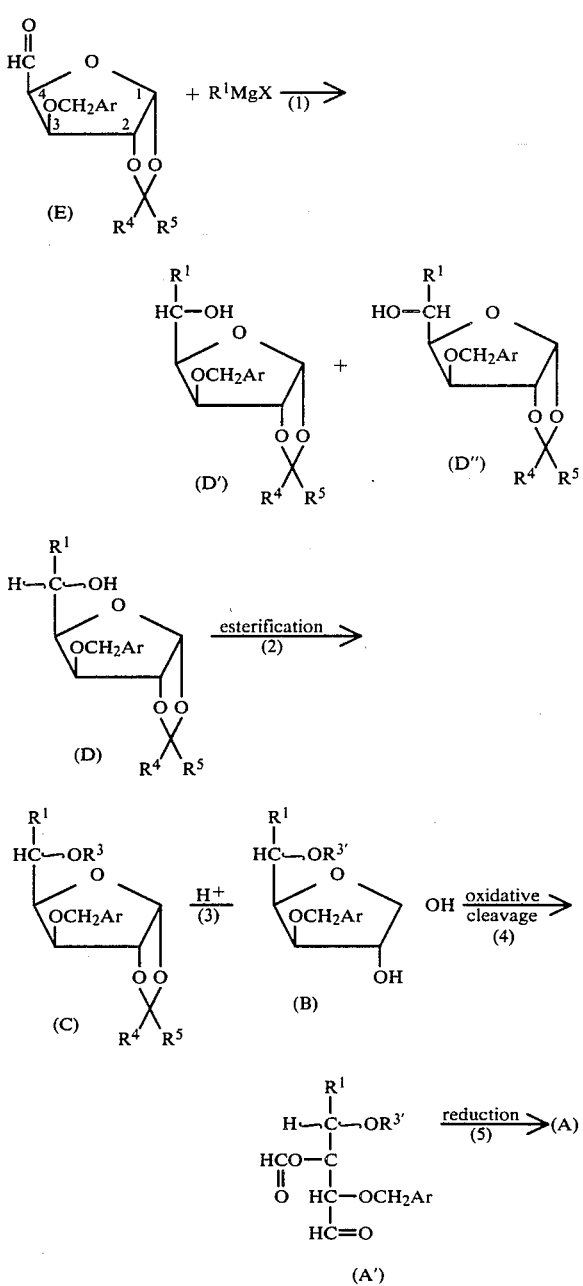

wherein X is halo, preferably bromo or iodo, $R^4$ and $R^5$ are independently hydrogen or lower alkyl, preferably methyl, and $R^1$, $R^3$ and the wavy $OR^{3'}$ are as defined hereinabove, and the wavy OH bond line in Formula B indicates α and/or β orientation of the 1-position hydroxy group.

The first step of this process can be effected by contacting the aldehyde (E) with a Grignard reagent, having the appropriate $R^1$ group, preferably in an inert organic solvent (preferably, ethyl ether). This step is typically conducted at temperatures in the range of about from 0° to 35° C., and conveniently is conducted by refluxing the reaction mixture for about from 1 to 10 hours. Suitable solvents which can be used include, for example, lower alkyl ethers (e.g., ethyl ether, propyl ether, butyl ether); tetrahydrofuran; methyltetrahydrofuran; dioxane, dimethoxymethane, dimethoxybutane, and the like and compatible mixtures thereof. Suitable Grignard reagents which can be used, include, for example, ethyl magnesium bromide, ethyl magnesium iodide, methyl magnesium bromide, methyl magnesium iodide, propyl magnesium chloride, and the like. Typically, about from 2 to 20, preferably 6 to 10 mole equivalents of Grignard reagent is used per mole of compound E. The resulting reaction product is a mixture of diastereoisomeric alcohols D' and D" which can be used as a mixture or if desired, the respective epimers D' and D" can be separated via any suitable procedure, for example, via crystallization or chromatography, etc. I have found that in many instances, the ido epimer (D') readily crystallizes out. In such cases it is thus convenient to use the ido epimer (D') as it is easily recovered in very pure form.

The starting materials of formula E are generally described in my U.S. Pat. No. 4,429,119.

In the second step of this process, intermediate D, which can be either epimer D' or D" or a mixture thereof, is esterified.

Preferably, the esterification is conducted by contacting the compound of Formula (D) with an acylating agent having the appropriate $R^{3'}$ substituent, such as, for example, the appropriate acyl chloride or bromide (i.e., $R^{3'}X$ where X is Cl or Br) or carboxylic acid anhydride [i.e. $(R^{3'})_2O$].

Where acyl halides are used, this reaction can be conveniently conducted by contacting compound D with the acyl halide, preferably in an inert organic solvent and in the presence of a scavenger base. Typically, this reaction is conducted at temperatures in the range of about from −78 to 100, preferably 0° to 25° C., for about from 1 to 48 hours, preferably 5 to 12 hours, using about from 1 to 5, preferably 1 to 1.2 moles of acyl halide per mole of compound (D). Suitable inert organic solvents which can be used include, for example, ethyl acetate, acetonitrile, methylene chloride, chloroform, diethyl ether, and the like and compatible mixtures thereof. Where a scavenger base is used typically about from 1 to 2 moles of base are used per mole of compound (D). Suitable scavenger bases which can be used include, for example, pyridine, triethylamine, methylpyridine, 4-dimethylaminopyridine and the like.

In the case where carboxylic acid anhydride is used, the reaction can be conveniently conducted by contacting compound (D) with the anhydride preferably in the presence of a scavenger base and optionally in an inert organic solvent. Typically, this reaction is conducted at temperatures in the range of about from −78 to 100, preferably 0° to 25° C., for about from 1 to 48 hours, preferably 5 to 12 hours, using about from 1 to 5, preferably 1 to 1.2 moles of anhydride per mole of compound (D). Suitable inert organic solvents which can be used, include, for example, ethyl acetate, acetonitrile, methylene chloride, chloroform, diethyl ether, and the like and compatible mixtures thereof. Where a scavenger base is used typically about from 1 to 2 moles of base are used per mole of compound (D). Suitable scavenger bases which can be used, include, for example, pyridine, triethylamine, methylpyridine, and the like.

In the third step of this process the 1,2-O-alkylidene group is cleaved. This can be effected by acid hydrolysis and typically is effected by mild acid hydrolysis, for example, by contacting compound (C) with aqueous trifluoroacetic acid, preferably at room temperature (about 20°–25° C.) for about 0.5–5 hours. Conveniently, the hydrolysis can also be conducted in other aqueous acids, such as for example, aqueous acetic acid, aqueous sulfuric acid, aqueous hydrochloric acid and the like, and compatible mixtures thereof. The product B is generally a mixture of alpha and beta anomers.

The fourth step can be conducted by contacting compound (B) with an oxidizing agent, preferably in an inert organic solvent, to effect ring oxidative cleavage of the 1 and 2 position hydroxy groups.

Typically, this process is conducted at temperatures in the range of about from −60° to 100° C., preferably about from 0° to 25° C., for about from 1 to 48 hours, preferably about 1 to 5 hours, using about from 1 to 5, preferably 1 to 1.2 moles of oxidizing agent per mole of compound (B). Suitable oxidizing agents which can be used, include, for example, alkali metal metaperiodates, periodic acid, lead tetraacetate and the like.

Suitable organic solvents which can be used, include, for example, methanol, ethanol, benzene, toluene, tetrahydrofuran, water and the like, and compatible mixtures thereof.

Generally, very good results are obtained using sodium metaperiodate as the oxidizing agent.

The fifth step of this process can be conducted by contacting compound (A') with a reducing agent preferably in an inert organic solvent.

Typically, this process is conducted at temperatures in the range of about from −60° to 75° C., preferably about from 0° to 25° C., for about from 1 to 24 hours, preferably about 2 to 5 hours, using about from 1 to 5, preferably 1 to 1.5 moles of oxidation agent per mole of compound (A'). Suitable reducing agents which can be used, include, for example, alkali metal borohydrides, sodium cyanoborohydride, and the like. Suitable inert organic solvents which can be used, include, for example, methanol, ethanol, isopropanol, diglyme, water, and the like, and compatible mixtures thereof.

Good results are generally obtained using sodium borohydride as the reducing agent.

The compounds of the invention wherein $R^3$ is hydrogen can be prepared via base hydrolysis of the corresponding acyloxy compounds:

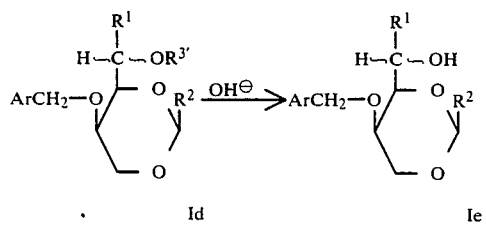

wherein Ar, $R^1$, $R^2$, $R^3$ and the ⌒ bond line are as defined hereinabove.

This process can be conveniently effected by contacting compound Id with a base, preferably in an inert organic solvent.

Typically, this process is conducted at temperatures in the range of about from 0° to 100° C., preferably 50° to 75° C., for about from 1 to 24 hours, preferably 1 to 5 hours, using about from 1 to 10, preferably 1.1 to 2 moles equivalent of base per mole of compound Id.

Suitable bases which can be used include, for example, alkali metal hydroxides (e.g., sodium hydroxide calcium hydroxide, potassium hydroxide), and the like.

Suitable inert organic solvents which can be used include, for example, methanol, ethanol, isopropanol, water and the like, and compatible mixtures thereof.

Conversely, the compounds of Formula Id can also be prepared via esterification of the corresponding compounds of Formula Ie:

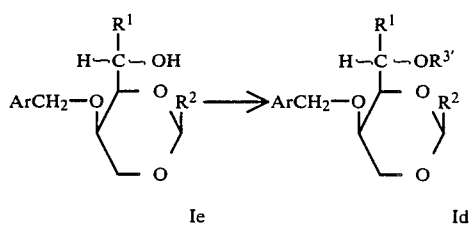

wherein Ar, R$^1$, R$^2$, R$^{3'}$ and the $\frown$ bond lines are as defined hereinabove.

The esterification can be effected in the same manner as described hereinabove with respect to the second step of the above-described process for preparing starting material A.

The Z is oxo compounds of the invention can in turn be prepared via oxidation of the hydroxy compounds Ie:

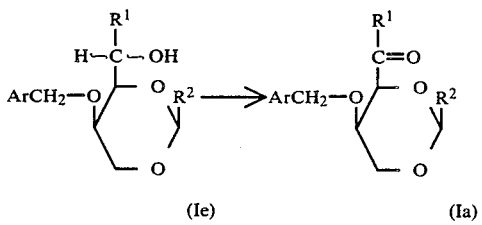

wherein Ar, R$^1$, R$^2$ and the wavy bond line are as defined hereinabove.

This process can be effected by contacting compound (Ie) with an oxidizing agent, preferably in an inert organic solvent.

Typically, this process is conducted at temperatures in the range of about from −25° to 100° C., preferably about from 0° to 25° C., for about from 1 to 24 hours, preferably about 2 to 5 hours, using about from 1 to 10, preferably 1.1 to 2 moles of oxidation agent per mole of compound (Ie). Suitable oxidizing agents which can be used, include, for example, chromium anhydride (CrO$_3$), sodium dichromate, pyridinium chlorochromate, and the like. Suitable inert organic solvents which can be used, include, for example, acetic acid, acetone, water, ether, methylene chloride, benzene, and the like, and compatible mixtures thereof.

Very good results are generally obtained using chromium anhydride as the oxidizing agent.

The compounds of Formula (Ie) can also be prepared via reductive alkylation of the corresponding aldehyde:

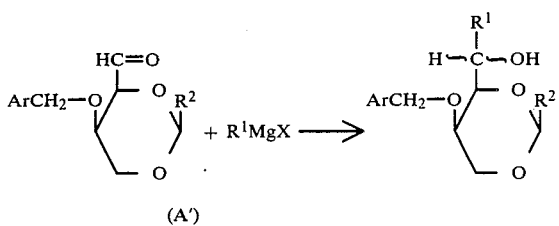

wherein Ar, R$^2$, R$^1$ and the bond lines are as defined hereinabove.

This process can be effected in the same manner as described hereinabove with respect to step 1 of the process for preparing starting material A.

The aldehyde (A') can be prepared from the tartrate ester via the following schematically represented process:

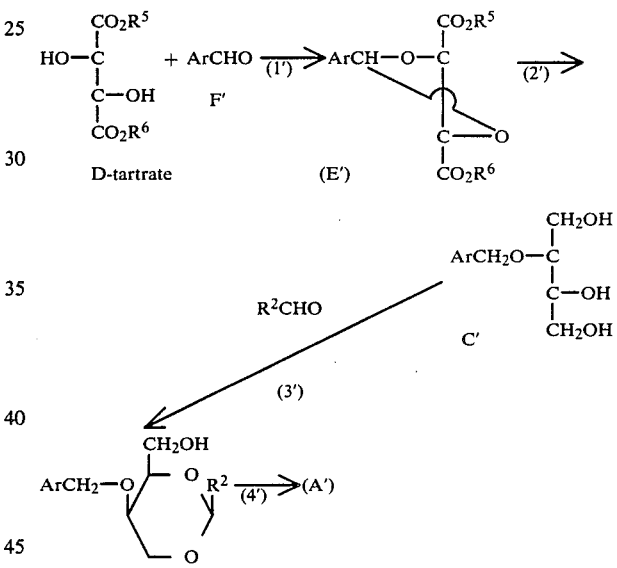

wherein Ar and R$^2$ are as defined hereinabove and R$^5$ and R$^6$ are independently lower alkyl or aryl (typically R$^5$ and R$^6$ are each methyl).

This process can be effected by contacting a D-tartrate ester, or a mixture of the D-tartrate with its L-tartrate isomer, with an aryl aldehyde (F'), having the desired Ar group, in the presence of an acid, under reactive conditions, preferably in an inert organic solvent.

Typically, this process is conducted at temperatures in the range of about from 25° to 150° C., preferably about from 50° to 125° C., (reflux temperature of solvent) for about from 5 to 100 hours, preferably about 24 to 48 hours, using about from 1 to 5, preferably 1 to 1.2 moles of compound (F) per mole of tartrate ester. Typically, about from 0.001 to 0.05 moles of acid are used per mole of tartrate esters.

Suitable acids which can be used, include, for example, p-toluenesulfonic acid, camphorsulfonic acid, hydrogen chloride, sulfuric acid, dry cation-exchange resin (H+ form) and the like.

Suitable inert organic solvents which can be used, include, for example, toluene, benzene, xylene, ether, methylene chloride, and the like, and compatible mixtures thereof.

The starting materials of Formula (F) are generally known materials and can be prepared by known procedures or obvious modifications thereof and are readily availble commercially. The tartrate esters are also known materials. Conveniently, dimethyl D-tartrate or a racemic mixture of the D isomer with its L-isomer can be used, since both products are readily commercially available. The above process is stereo selective to the starting material. Thus, the D-tartrate ester yields the corresponding 2S-(2$\beta$,4,$\beta$,5$\beta$) isomer of the present invention whereas the L-tartrate yields the virtually inactive 2R-(2$\beta$,4$\beta$,5$\beta$) isomer. Thus, where a racemic tartrate mixture is used, the product will be a mixture of the active and inactive isomers which can be used as is, or if desired subjected to resolution procedures. Resolution can also be effected as an intermediate step.

The second step (2') involving reductive cleavage of the benzylidene acetal can be effected by contacting intermediate E' with a reducing agent and a Lewis acid. This is conveniently conducted in two steps by first contacting compound E' with a reducing agent, under reactive conditions, and then contacting the reduced product with a Lewis acid. Typically, both steps are conducted in an inert organic solvent and can be conveniently conducted in situ.

Typically, the reductive portion of step 2' is conducted at temperatures in the range of about from 0° to 100° C., preferably about from 25° to 50° C., for about from 0.5 to 10 hours, preferably about 1 to 2 hours, using about from 2 to 10, preferably 2 to 4 moles of reducing agents per mole of compound (E'). A suitable reducing agent which can be used, include, for example, lithium aluminum hydride.

Suitable organic solvents which can be used, include, for example, ethyl ether, methylene chloride, chloroform, propyl ether, and the like, and compatible mixtures thereof.

Typically, the ring cleavage of step 2' is conducted at temperatures in the range of about from 0° to 100° C., preferably about 25° to 50° C., for about from 0.5 to 10 hours, preferably about 1 to 2 hours, using about from 1 to 5, preferably 1 to 1.2 moles of Lewis acid per mole of compound (E'). A suitable Lewis acid which can be used, include, for example, anhydrous aluminum chloride. The same inert organic, solvents as indicated above for the reductive step are also suitable for this reaction.

Alternatively, the second step (2') can be effected by contacting intermediate E' with diisobutylaluminum hydride in one step. [See Chemistry Letters, 1593 (1983)].

Typically, this reductive cleavage with diisobutylaluminum hydride is conducted at temperatures in the range of about from −50° to 100° C., preferably about from 0° to 25° C. for about 1 to 24 hours, preferably about 2 to 5 hours using about from 5 to 10, preferably 5 to 7 moles of the reducing agent per mole of compound (E').

Suitable organic solvents which can be used include, for example, benzene, toluene, xylene, and the like, and compatible mixtures thereof.

The third step (3') of this process can be effected by contacting intermediate C' with an aldehyde having the desired $R^2$ group. This step can be conducted in the same manner as described hereinabove with respect to the preparation of compound Id via the reaction of compound A with aldehyde B. However, in this step this process affords a mixture of the 1,3-dioxane and 1,3-dioxolane derivatives with the latter predominating which can be isomerized to the former in the presence of an acid catalyst with or without inert organic solvents. I have found that in many instances, the isomerization is best carried out with camphorsulfonic acid without any inert solvents. Under these conditions, the equilibrium between the 1,3-dioxane and the 1,3-dioxolane is strongly displaced in favor of the formation of the former.

The last step of this process, step (4') can be effected by contacting compound (B') with an oxidizing agent, preferably in an inert organic solvent.

Typically, this process is conducted at temperatures in the range of about from −75° to 25° C., preferably about from −60° to −50° C., for about from 0.5 to 10 hours, preferably about 0.5 to 2 hours, using about from 1 to 5, preferably 1.1 to 1.5 moles of oxidizing agent per mole of compound (B'). Suitable oxidizing agents which can be used, include, for example, dimethyl sulfoxide-oxalyl chloride, pyridinium chlorochromate, dimethyl sulfoxide-trifluoroacetic anhydride, pyridine —$SO_3$— dimethyl sulfoxide, and the like. Suitable inert organic solvents which can be used, include, for example, methylene chloride and chloroform, and the like, and compatible mixtures thereof.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl.

The term "lower alkylene" refers to both straight chained and branched chained alkylene groups having 1 through 6 carbon atoms, preferably 1 through 4 carbon atoms and includes, for example,

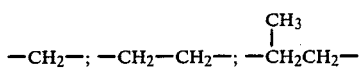

and the like.

The term "lower alkenyl" refers to alkenyl groups having 2 through 6, preferably 2 through 4, carbon atoms and includes, for example, vinyl, 1-propenyl, 2-propenyl, 1-butenyl, 2-methylprop-1-enyl and the like.

The term "lower alkoxy" refers to the group —OR′ wherein R′ is lower alkyl.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "arylalkylene" refers to the group ArR$^3$— wherein Ar is aryl and R$^3$ is alkylene having 1 through 3 carbon atoms and includes both straight-chained and branched-chained alkylenes, for example, methylene, ethyl, 1-methylethyl, and propyl.

The term "room temperature" or "ambient temperature" refers to about 20°-25° C.

Utility

The compounds of Formula (I) exhibit both pre-emergence and post-emergence herbicidal activity and exhibit especially good pre-emergence herbicidal activity.

Also, by proper adjustment of application rates, certain of the compounds can be safely used for pre-emergence control of grassy weeds in certain broad-leaf crops, such as soybean, alfalfa, cotton, and peanuts.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the climate and general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for preemergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Example(s). Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

Example 1

1,2:5,6-di-O-isopropylidene-3-O-(2′-chlorobenzyl)-α-D-glucofuranose

In this example 24.0 g (0.60 mole) of sodium hydride in the form of a 60 wt. % mixture with mineral oil, were slowly added under a nitrogen atmosphere to a solution containing 130 g (0.50 mole) of 1,2:5,6-di-O-isopropylidene-α-D-glucofuranose in 800 ml of tetrahydrofuran. Two grams of tetrabutylammonium iodide were then added to this mixture followed by dropwise addition of 88.5 g (0.55 moles) of 2-chlorobenzyl chloride. The reaction mixture was then stirred overnight (about 15 hours) at room temperature. A thin layer chromatography (THF-hexanes 1:2) indicated the reaction to be complete and was quenched with the slow addition of ethanol. The reaction mixture was concentrated by evaporation under reduced pressure affording a viscous mixture which was then dissolved in one liter of methylene chloride and 500 ml of water. The organic layer was separated and treated with 250 ml of water and dilute acetic acid to neutralize the mixture. The organic layer was then washed with a saturated solution of sodium chloride, dried over anhydrous magnesium sulfate and concentrated by evaporation under reduced pressure to afford 191 g (99% yield) of the title compound as a pale yellow liquid.

Example 2

1,2-O-isopropylidene-3-O-(2′-chlorobenzyl)-α-D-glucofuranose

In this example, 191 g (0.50 mole) of 1,2:5,6-di-O-isopropylidene-3-O-(2′-chlorobenzyl)-α-D-glucofuranose was stirred in a mixture of 575 ml of acetic acid and 325 ml of water at 40°–45° C. overnight (about 18 hours). The reaction was monitored by thin layer chromatography. The reaction mixture was concentrated by evaporation under reduced pressure at 55°–60° C., dissolved in 1 liter of methylene chloride, washed twice with water and then with a saturated sodium chloride solution. The organic extract was dried over anhydrous magnesium sulfate and concentrated by evaporation under reduced pressure to afford 169 g (97% yield) of the title compound as a yellow viscous liquid.

Example 3

1,2-O-isopropylidene-3-O-(2′-chlorobenzyl)-α-D-xylopentodialdo-1,4-furanose

In this example a solution of 80 g (0.23 mole) of 1,2-O-isopropylidene-3-O-(2′-chlorobenzyl)-α-D-glucofuranose in 750 ml of absolute methanol was stirred in an ice-water bath, and 55.6 g (0.26 mole) of sodium metaperiodate in 750 ml of water was added dropwise. after the addition had been completed, the solution was stirred 2 hrs. at 0°. Ethylene glycol (10 ml) was added to decompose any excess oxidant and the methanol was evaporated off. The aqueous mixture was treeated with methylene chloride, washed with water, dried over anhydrous magnesium sulfate and concentrated by evaporation under reduced pressure to afford 70.1 g (97% yield) of the title compound as a yellow liquid.

Example 4

1,2-O-isopropylidene-3-O-(2′-chlorobenzyl)-6-deoxy-β-L-idofuranose

In this example a solution of 70.9 g (0.23 mole) of 1,2-O-isopropylidene-3-O-(2′-chlorobenzyl)-α-D-xylopentodialdo-1,4-furanose in 1 liter of anhydrous ethyl ether was added dropwise to an ether solution of methyl magnesium iodide which had been prepared by the addition of 87.5 ml (1.4 moles) of methyl iodide to a mixture of 39 g (1.6 moles) of magnesium turnings and 1.25 liters of anhydrous ethyl ether. The reaction mixture was refluxed for 2 hours, cooled and poured into 1 liter of 25 wt. % aqueous ammonium chloride. Ether (500 ml) was added, and the organic phase was separated, washed with a saturated solution of sodium chloride and dried over anhydrous magnesium sulfate. Concentration by evaporation under reduced pressure afforded a semi-solid. Recrystallization from ethanol-ligroin (bp 30°–60°) afforded 44.2 g (59% yield) of the title compound as a white crystalline solid.

Example 5

1,2-O-isopropylidene-5-O-benzoyl-3-O-(2′-chlorobenzyl)-6-deoxy-β-L-idofuranose

In this example 52 g (0.37 mole) of benzoyl chloride was added dropwise to a solution of 109.6 g (0.33 mole) of 1,2-O-isopropylidene-3-O-(2′-chlorobenzyl)-6-deoxy-β-L-idofuranose in 300 ml of pyridine. The reaction mixture was stirred 4 hours at room temperature and was poured into 1 liter of methylene chloride and 500 ml of water. The organic layer was separated, washed with dilute aqueous hydrochloric acid to remove pyridine, followed by washing with a saturated solution of sodium chloride and dried over anhydrous magnesium sulfate. Concentration by evaporation under reduced pressure gave a solid which was recrystallized by dissolving in a minimum amount of hot ethanol followed by addition of ligroin (bp 30°–90°) to afford 118.1 g (82% yield) of the title compound with mp 112°–117° C.

Example 6

2-O-Benzoyl-4-O-(2′-chlorobenzyl)-1-deoxy-D-xylitol

In this example a solution of 118 g (0.27 mole) of 1,2-O-isopropylidene-5-O-benzoyl-3-O-(2′-chlorobenzyl)-6-deoxy-β-L-idofuranose in 1.5 liter of aqueous acetic acid (70%) was refluxed for 4 hours. The reaction mixture was concentrated by evaporation under reduced pressure and was treated with 1 liter of methylene chloride. The organic layer was separated, washed with 10% sodium hydroxide until neutral, followed by a saturated solution of sodium chloride and concentrated by evaporation under reduced pressure.

To a solution of the above residue in 1.25 liter of methanol cooled in an ice-water bath was added dropwise, a solution of 66 g (0.31 mole) of sodium metaperiodate in 750 ml of water in 0.5 hour. The resulting suspension was stirred 1 hour at room temperature and extracted into methylene chloride. The organic layer was then washed with a saturated solution of sodium chloride, dried over anhydrous magnesium sulfate and concentrated by evaporation under reduced pressure.

To a solution of the preceding product in 1.25 liter of absolute ethanol, cooled in an ice-water bath was added portionwise 14.5 g (0.38 mole) of sodium borohydride for 0.5 hour. The resulting solution was stirred for 2 hours, cooled and neutralized with 5% hydrochloric acid by dropwise addition. The mixture was concentrated by evaporation under reduced pressure at 40°–50° C., dissolved in 1 liter of methylene chloride, washed with aqueous sodium hydroxide (1N) followed by dilute hydrochloric acid and saturated sodium chloride. Concentration by evaporation under reduced pressure gave a solid which was recrystallized by dissolving in a minimum amount of hot ethanol followed by addition of hexane to afford 60.3 g (61% yield) of the title compound with mp 80°–83° C.

Example 7

2S-[2β,4β(S),5β]-4-(1-benzoyloxyethyl)-5-(2'-chlorobenzyloxy)-2-ethyl-1,3-dioxane In this example a solution of 36.5 g (0.1 mole) of 2-O-benzoyl-4-O-(2'-chlorobenzyl)-1-deoxy-D-xylitol in 1.2 liter of toluene was mixed with 1.5 g of p-toluenesulfonic acid, 10 g (0.17 mole) of propionaldehyde and 40 g of anhydrous copper sulfate. The reaction mixture was stirred for 4 hours at room temperature. Examination by thin layer chromatography showed completion of the reaction. The mixture was filtered, and the solids were washed with diethyl ether. The combined organic layer was then washed with dilute sodium hydroxide to neutralize the catalyst, followed with a saturated solution of sodium chloride, dried over anhydrous magnesium sulfate and concentrated by evaporation under reduced pressure. The above procedure was repeated and the combined product was recrystallized from ligroin (bp 60°–90° C.) to afford 66.1 g (82% yield) of the title compound as a white solid with mp 50°–52° C.

Similarly, by applying the above procedure using the corresponding $R^2$ aldehyde, the following compounds can be prepared:

2S-[2β,4β(S),5β]-4-(1-benzoyloxyethyl)-5-(2'-chlorobenzyloxy)-2-methyl-1,3-dioxane;
2S-[2β,4β(S),5β]-4-(1-benzoyloxyethyl)-5-(2'-chlorobenzyloxy)-2-butyl-1,3-dioxane; and
2S-[2β,4β(S),5β]-4-(1-benzoyloxyethyl)-5-(2'-chlorobenzyloxy)-2-hexyl-1,3-dioxane.

Similarly, by adopting the above procedure to the corresponding 2-O-substituted-4-O-substituted-1-deoxy-D-xylitol compounds, which in turn can be prepared by adopting the procedures of Examples 1–6, using the appropriate 3-O-arylmethyl-α-D-glucofuranose starting materials in Example 1 and the corresponding alkyl Grignard reagent and acyl halide in Examples 4 and 6 respectively, the following compounds can be prepared:

2S-[2β,4β(S),5β]-4-(1-benzoyloxyethyl)-5-(2'-fluorobenzyloxy)-2-ethyl-1,3-dioxane;
2S-[2β,4β(S),5β]-4-(1-benzoyloxyethyl)-5-(2'-trifluoromethylbenzyloxy)-2-ethyl-1,3-dioxane;
2S-[2β,4β(S),5β]-4-(1-benzoyloxyethyl)-5-(2',6'-dimethylbenzyloxy)-2-ethyl-1,3-dioxane;
2S-[2β,4β(S),5β]-4-(1-benzoyloxyethyl)-5-(4'-methoxybenzyloxy)-2-ethyl-1,3-dioxane;
2S-[2β,4β(S),5β]-4-(1-benzoyloxyethyl)-5-(2'-bromo-3'-iodobenzyloxy)-2-ethyl-1,3-dioxane;
2S-[2β,4β(S),5β]-4-(1-benzoyloxyethyl)-5-(3'-ethoxy-4'-trifluoromethylbenzyloxy)-2-ethyl-1,3-dioxane;
2S-[2β,4β(S),5β]-4-(1-benzoyloxyethyl)-5-(2'-methyl-5'-fluorobenzyloxy)-2-ethyl-1,3-dioxane;
2S-[2β,4β(S),5β]-4-(1-benzoyloxyethyl)-5-(thien-2-yl)oxy-2-ethyl-1,3-dioxane;
2S-[2β,4β(S),5β]-4-(1-benzoyloxyethyl)-5-(pyrid-3-yl)oxy-2-ethyl-1,3-dioxane;
2S-[2β,4β(S),5β]-4-(1-acetyloxyethyl)-5-(2'-chlorobenzyloxy)-2-ethyl-1,3-dioxane;
2S-[2β,4β(S),5β]-4-(1-propionyloxyethyl)-5-(2'-fluorobenzyloxy)-2ethyl-1,3-dioxane;
2S-[2β,4β(S),5β]-4-(1-valeryloxypropyl)-5-(4'-hexylbenzyloxy)-2-ethyl-1,3-dioxane;
2S-[2β,4β(S),5β]-4-[1-(2',4'-dichlorophenoxyacetyl)oxybutyl]-5-(2',6'-dimethylbenzyloxy)-2-ethyl-1,3-dioxane;
2S-[2β,4β(S),5β]-4-[1-(2'-fluorophenoxyacetyl)oxypentyl]-5-(thien-3-yl)oxy-2-ethyl-1,3-dioxane;
2S-[2β,4β(S),5β]-4-[1-(4'-trifluoromethyl-2'-chlorophenoxyacetyl)oxypropyl]-5-(pyrid-1-yl)oxy-2-ethyl-1,3-dioxane;
2S-[2β,4β(S),5β]-4-(1-benzoyloxyethyl)-5-(2'-fluorobenzyloxy)-2-methyl-1,3-dioxane;
2S-[2β,4β(S),5β]-4-(1-benzoyloxyethyl)-5-(2'-trifluoromethylbenzyloxy)-2-butyl-1,3-dioxane;
2S-[2β,4β(S),5β]-4-(1-benzoyloxyethyl)-5-(2',6'-dimethylbenzyloxy)-2-hexyl-1,3-dioxane;
2S-[2β,4β(S),5β]-4-(1-benzoyloxyethyl)-5-(4'-methoxybenzyloxy)-2-methyl-1,3-dioxane;
2S-[2β,4β(S),5β]-4-(1-benzoyloxyethyl)-5-(2'-bromo-3'-iodobenzyloxy)-2-t-butyl-1,3-dioxane;
2S-[2β,4β(S),5β]-4-(1-benzoyloxyethyl)-5-(3'-ethoxy-4'-trifluoromethylbenzyloxy)-2-hexyl-1,3-dioxane;
2S-[2β,4β(S),5β]-4-(1-benzoyloxyethyl)-5-(2'-methyl-5'-fluorobenzyloxy)-2-methyl-1,3-dioxane;
2S-[2β,4β(S),5β]-4-(1benzoyloxyethyl)-5-(thien-2-yl)oxy-2-t-butyl-1,3dioxane;
2S-[2β,4β(S),5β]-4-(1-benzoyloxyethyl)-5-(pyrid-3-yl)oxy-2-hexyl-1,3-dioxane;
2S-[2β,4β(S),5β]-4-(1-acetyloxyethyl)-5-(2'chlorobenzyloxy)-2-methyl-1,3-dioxane;
2S-[2β,4β(S),5β]-4-(1-propionyloxyethyl)-5-(2'-fluorobenzyloxy)-2-t-butyl-1,3-dioxane;
2S-[2β,4β(S),5β]-4-(1-valeryloxypropyl)-5-(4'-hexylbenzyloxy)-2-hex-1'-yl-1,3-dioxane;
2S-[2β,4β(S),5β]-4-[1-(2',4'-dichlorophenoxyacetyl)oxybutyl]-5-(2',6'-dimethylbenzyloxy)-2-methyl-1,3-dioxane;
2S-[2β,4β(S),5β]-4-[1-(2'-fluorophenoxyacetyl)oxypentyl]-5-(thien-3-yloxy)-2-t-butyl-1,3-dioxane; and
2S-[2β,4β(S),5β]-4-[1-(4'-trifluoromethyl-2'-chlorophenoxyacetyl)oxypropyl]-5-pyrid-1-yloxy-2-hexyl-1,3-dioxane.

Example 8

2S-[2β,4β(S),5β]-5-(2'-chlorobenzyloxy)-2-ethyl-4-(1-hydroxyethyl)-1,3-dioxane

In this example a solution of 12 g (0.03 mole) of 2S-[2β,4β(S),5β]-4-(1-benzoyloxyethyl)-5-(2'-chlorobenzyloxy)-2-ethyl-1,3-dioxane and 1.8 g (0.045 mole) of sodium hydroxide in 200 ml of water and 600 ml of methanol was refluxed for 2 hours. The reaction mixture was cooled, neutralized with dilute hydrochloride acid and concentrated by evaporation under reduced pressure. The residue was treated with methylene chloride and washed with dilute sodium hydroxide, followed by saturated sodium chloride. Concentration by evaporation under reduced pressure gave a solid which was recrystallized from ligroin (bp 60–90) to afford 8.2 g (92% yield) of the title compound with mp 81°–83° C.

Similarly, by applying the above procedure using the compounds illustrated in Example 7 as starting materials, the following compounds can be made:

2S-[2β,4β(S),5β]-4-(1-hydroxyethyl)-5-(2'-chlorobenzyloxy)-2-methyl-1,3-dioxane;

2S-[2β,4β(S),5β]-4-(1-hydroxyethyl)-5-(2'-chlorobenzyloxy)-2-t-butyl-1,3-dioxane;

2S-[2β,4β(S),5β]-4-(1-hydroxyethyl)-5-(2'-chlorobenzyloxy)-2-hexyl-1,3-dioxane;

2S-[2β,4β(S),5β]-4-(1-hydroxyethyl)-5-(2'-fluorobenzyloxy)-2-methyl-1,3-dioxane;

2S-[2β,4β(S),5β]-4-(1-hydroxyethyl)-5-(2'-trifluoromethylbenzyloxy)-2-t-butyl-1,3-dioxane;

2S-[2β,4β(S),5β]-4-(1-hydroxyethyl)-5-(2',6'-dimethylbenzyloxy)-2-hexyl-1,3-dioxane;

2S-[2β,4β(S),5β]-4-(1-hydroxyethyl)-5-(4'-methoxybenzyloxy)-2-methyl-1,3-dioxane;

2S-[2β,4β(S),5β]-4-(1-hydroxyethyl)-5-(2'-bromo-3'-iodobenzyloxy)-2-t-butyl-1,3-dioxane;

2S-[2β,4β(S),5β]-4-(1-hydroxyethyl)-5-(3'-ethoxy-4'-trifluoromethylbenzyloxy)-2-hexyl-1,3-dioxane;

2S-[2β,4β(S),5β]-4-(1-hydroxyethyl)-5-(2'-methyl-5'-fluorobenzyloxy)-2-methyl-1,3-dioxane;

2S-[2β,4β(S),5β]-4-(1-hydroxyethyl)-5-(thien-2-yl)oxy-2-t-butyl,3-dioxane;

2S-[2β,4β(S),5β]-4-(1-hydroxypropyl)-5-(4'-hexylbenzyloxy)-2-hexyl-1,3-dioxane;

2S-[2β,4β(S),5β]-4-(1-hydroxybutyl)-5-(2',6'-dimethylbenzyloxy-2-methyl-1,3-dioxane;

2S-[2β,4β(S),5β]-4-(1-hydroxypentyl)-5-(thien-3-yl)oxy-2-t-butyl-1,3-dioxane; and 2S-[2β,4β(S),5β]-4-(1-hydroxypropyl)-5-(pyrid-1'-yl)oxy-2-2-hexyl-1,3-dioxane;

EXAMPLE 9

2S-(2β,4β,5β)-4-acetyl-5-(2'-chlorobenzyloxy)-2-ethyl-1,3-dioxane

In this example a solution of 3.0 g (0.03 mole) of chronic anhydride in 30 ml of water-acetic acid (1:4 mol) was added dropwise to a cooled solution of 4.5 g (0.015 mole) of 2S-[2β,4β(S),5β]-5-(2'-chlorobenzyloxy)-2-ethyl-4-(1-hydroxyethyl)-1,3-dioxane in 25 ml of acetic acid. The reaction mixture was stirred 2 hours at room temperature and was treated with methylene chloride and water. The organic layer was separated, washed with dilute aqueous sodium carbonate, followed by a saturated solution of sodium chloride. The organic extract was dried over anhydrous magnesium sulfate and concentrated by evaporation under reduced pressure to afford 3.7 g (83% yield) of the title compound as a colorless liquid which was chromatographed by flash column chromatography employing methylene chloride as the eluent.

Similarly, by applying the above procedure, using the compounds illustrated in Example 8 as starting materials, the corresponding 4-acyl compounds can be prepared, for example:

2S-(2β,4β,5β)-4-acetyl-5-(2'-chlorobenzyloxy)-2-methyl-1,3-dioxane;

2S-(2β,4β,5β)-4-acetyl-5-(2'-chlorobenzyloxy)-2-t-butyl-1,3-dioxane;

2S-(2β,4β,5β)-4-acetyl-5-(2'-chlorobenzyloxy)-2-hexyl-1,3-dioxane;

2S-(2β,4β,5β)-4-acetyl-5-(2'-fluorobenzyloxy)-2-methyl-1,3-dioxane;

2S-(2β,4β,5β)-4-acetyl-5-(2'-trifluoromethylbenzyloxy)-2-t-butyl-1,3-dioxane;

2S-(2β,4β,5β)-4-acetyl-5-(2',6'-dimethylbenzyloxy)-2-hexyl-1,3-dioxane.

EXAMPLE 10

(4S,5S)-Dimethyl 2-(2-chlorophenyl)-1,3-dioxolane-4,5-dicarboxylate

In this example 50.0 g (0.28 mole) of dimethyl D-tartrate and 39.5 g (0.28 mole) of 2-chlorobenzaldehyde were refluxed for 48 hours in 500 ml of toluene in the presence of 0.2 g of p-toluenesulfonic acid. Water was azeotroped off with the aid of a Dean-Stark trap. The reaction mixture was concentrated by evaporation under reduced pressure to afford 50.8 g (60% yield) of the title compound as a solid which was washed with hexane and ether.

EXAMPLE 11

2-O-(2-chlorobenzyl)-D-threitol

In this example 11.4 g (0.30 mole) of lithium aluminum was added under a nitrogen atmosphere to a solution of 41.0 g (0.14 mole ) of (4S,5S)-dimethyl 2-(2-chloro)phenyl-1,3-dioxolane-4,5-dicarboxylate in 2 liters of ethyl ether-methylene chloride (1:1 by volume) in 1-gram portions during 15 minutes. A vigorous exotherm was observed and the reaction mixture was stirred another 5 minutes. Anhydrous aluminum chloride 20.0 g (0.15 mole) was then introduced in small portions during 10–15 minutes, and the reaction mixture was refluxed 4 hours. After cooling, the reaction mixture was treated with dropwise addition of 80 ml of water, followed by 80 ml of 10% aqueous sodium hydroxide. The reaction mixture was filtered through diatomaceous earth and the granular precipitate was extracted into hot ethyl acetate. The ethyl acetate extract was then combined with the initial ethyl-methylene chloride filtrate and was concentrated to afford 27.2 g (81% yield) of the title compound as a white solid with mp 88°–88.5° C.

EXAMPLE 12

2S-(2β,4β,5β)-5-(2'-chlorobenzyloxy)-4-hydroxymethyl-2-propyl-1,3-dioxane

In this example a solution of 20.0 g (0.08 mole) of 2-O-(2'-chlorobenzyl)-D-threitol in 200 ml of toluene was mixed with 0.2 g of p-toluenesulfonic acid, 8.8 g (0.12 mole) of butyraldehyde and 30 g of anhydrous copper sulfate. The reaction mixture was stirred for 5 hours at room temperature. The mixture was filtered and the filtrate was washed with 5% aqueous sodium hydroxide and a saturated solution of sodium chloride. The solvent was removed by concentration under reduced pressure and the residue was chromatographed on a silica gel column employing acetone-toluene (1:10) as eluent to afford 1.2 g of the title compound as a white solid with mp 75°–76° C.

EXAMPLE 13

2S-(2β,4β,5β)-5-(2'-chlorobenzyloxy)-2-propyl-1,3-dioxane-4-carboxaldehyde

In this example a solution of 6.8 ml (0.088 mole) of dimethyl sulfoxide in 20 ml of methylene chloride was added to a solution of 4 ml (0.044 mole) of oxalyl chloride in 100 ml of methylene chloride kept at −50° to −60° C. by means of a dry ice-acetone bath. The above reaction mixture was stirred for 2 minutes and a solution of 12 g (0.04 mole) of 2S-(2β,4β,5β)-5-(2'-chlorobenzyloxy)-4-(hydroxymethyl)-2-propyl-1,3-dioxane in 40 ml of methylene chloride was added dropwise within 5 minutes. The solution was stirred for 1.5 hours and then 28 ml (0.20 mole) of triethylamine was introduced and the reaction mixture was allowed to warm to room temperature. The reaction product was then extracted into methylene chloride and washed consecutively with water, dilute hydrochloric acid , dilute sodium hydroxide, and a saturated solution of sodium chloride. After drying over anhydrous magnesium sulfate, the solution was concentrated by evaporation under reduced pressure to afford 11.6 g (97% yield) of the title compound as a yellow liquid.

EXAMPLE 14

2S-[2β,4β(RS),5β]-5-(2'-chlorobenzyloxy)-4-(1-hydroxyethyl)-2-propyl-1,3-dioxane;

In this example a solution of 6.0 g (0.02 mole) of 2S-(2β,4β,5β)-5-(2'-chlorobenzyloxy)-2-propyl-1,3-dioxane-4-carboxaldehyde in 50 ml of anhydrous ethyl ether was added dropwise to an ether solution of methyl magnesium iodide which had been prepared by the addition of 19.9 g (0.14 mole) of methyl iodide to a mixture of 4.1 g (0.17 mole) of magnesium turnings and 100 ml of anhydrous ethyl ether. The reaction mixture was refluxed for 2 hours, cooled and poured into 50 wt. % aqueous ammonium chloride. Ether was added, and the organic phase was separated, washed with a saturated solution of sodium chloride and dried over anhydrous magnesium sulfate. Concentration by evaporation under reduced pressure afforded the product. Recrystallization from ethanolligroin (bp 60°–90°) afforded 4.7 g (74% yield) of the title compound as a white crystalline material with mp 67°–68° C.

Similarly, by applying the above procedure using the corresponding ArCH₂O-R² aldehyde starting materials (which can be prepared by applying the procedures of Examples 10 and 12 using the corresponding Ar aldehyde in Example 10 and the corresponding R² aldehyde in Example 12), the following compounds can be prepared:

2S-[2β,4β(RS),5β]-5-(2'-fluorobenzyloxy)-4-(1-hydroxyethyl)-2-propyl-1,3-dioxane;
2S-[2β,4β(RS),5β]-5-(2'-trifluoromethylbenzyloxy)-4-(1-hydroxyethyl)-2-propyl-1,3-dioxane;
2S-[2β,4β(RS),5β]-5-(2',6'-dimethylbenzyloxy)-4-(1-hydroxyethyl)-2-propyl-1,3-dioxane;
2S-[2β,4β(RS),5β]-5-(2'-methoxybenzyloxy)-4-(1-hydroxyethyl)-2-propyl-1,3-dioxane;
2S-[2β,4β(RS),5β]-5-(4'-iodobenzyloxy)-4-(1-hydroxyethyl)-2-propyl-1,3-dioxane;
2S-[2β,4β(RS),5β]-5-(3'-propylbenzyloxy)-4-(1-hydroxyethyl)-2-propyl-1,3-dioxane;
2S-[2β,4β(RS),5β]-5-[2'-(2,2-dichloroethyl)benzyloxy]-4-(1-hydroxyethyl)-2-propyl-1,3-dioxane;
2S-[2β,4β(RS),5β]-5-(3'-chloro-4'-iodobenzyloxy)-4-(1-hydroxyethyl)-2-propyl-1,3-dioxane;
2S-[2β,4β(RS),5β]-5-(2',5'-dimethylbenzyloxy)-4-(1-hydroxyethyl)-2-propyl-1,3-dioxane;
2S-[2β,4β(RS),5β]-5-(3'-trifluoromethyl-6'-propylbenzyloxy)-4-(1-hydroxyethyl)-2-propyl-1,3-dioxane;
2S-[2β,4β(RS),5β]-5-(2'-fluoro-3'-ethylbenzyloxy)-4-(1-hydroxyethyl)-2-propyl-1,3-dioxane;
2S-[2β,4β(RS),5β]-5-(2'-iodo-4'-trifluoromethylbenzyloxy)-4-(1-hydroxyethyl)-2-propyl-1,3-dioxane;
2S-[2β,4β(RS),5β]-5-(3',5'-dichlorobenzyloxy)-4-(1-hydroxyethyl)-2-propyl-1,3-dioxane;
2S-[2β,4β(RS),5β]-5-(2'-chlorobenzyloxy)-4-(1-hydroxyethyl)-2-isopropyl-1,3-dioxane;
2S-[2β,4β(RS),5β]-5-(2'-fluorobenzyloxy)-4-(1-hydroxyethyl)-2-isopropyl-1,3-dioxane;
2S-[2β,4β(RS),5β]-5-(2'-trifluoromethylbenzyloxy)-4-(1-hydroxyethyl)-2-isopropyl-1,3-dioxane;
2S-[2β,4β(RS),5β]-5-(2',6'-dimethylbenzyloxy)-4-(1-hydroxyethyl)-2-isopropyl-1,3-dioxane;
2S-[2β,4β(RS),5β]-5-(2'-methoxybenzyloxy)-4-(1-hydroxyethyl)-2-isopropyl-1,3-dioxane;
2S-[2β,4β(RS),5β]-5-(4'-iodobenzyloxy)-4-(1-hydroxyethyl)-2-isopropyl-1,3-dioxane;
2S-[2β,4β(RS),5β]-5-(3'-propylbenzyloxy)-4-(1-hydroxyethyl)-2-isopropyl-1,3-dioxane;
2S-[2β,4β(RS),5β]-5-[2'-(2,2-dichloroethyl)benzyloxy]-4-(1-hydroxyethyl)-2-isopropyl-1,3-dioxane;
2S-[2β,4β(RS),5β]-5-(3'-chloro-4'-iodobenzyloxy)-4-(1-hydroxyethyl)-2-isopropyl-1,3-dioxane;
2S-[2β,4β(RS),5β]-5-(2',5'-dimethylbenzyloxy)-4-(1-hydroxyethyl)-2-isopropyl-1,3-dioxane;
2S-[2β,4β(RS),5β]-5-(3'-trifluoromethyl-6'-propylbenzyloxy)-4-(1-hydroxyethyl)-2-isopropyl-1,3-dioxane;
2S-[2β,4β(RS),5β]-5-(2'-fluoro-3'-ethylbenzyloxy)-4-(1-hydroxyethyl)-2-isopropyl-1,3-dioxane;
2S-[2β,4β(RS),5β]-5-(2'-iodo-4'-trifluoromethylbenzyloxy)-4-(1-hydroxyethyl)-2-isopropyl-1,3-dioxane;
2S-[2β,4β(RS),5β]-5-(3',5'-dichlorobenzyloxy)-4-(1-hydroxyethyl)-2-isopropyl-1,3-dioxane.

Similarly, by applying the above procedure using magnesium iodide, propyl magnesium iodide and n-butyl magnesium iodide in place of methyl magnesium iodide that corresponding 4-(1-hydroxyalkyl) homologs of the above compounds can be prepared, for example:
2S-[2β,4β(RS),5β]-5-(2'-chlorobenzyloxy)-4-(1-hydroxypropyl)-2-propyl-1,3-dioxane;
2S-[2β,4β(RS),5β]-5-(2'-fluorobenzyloxy)-4-(1-hydroxybutyl)-2-propyl-1,3-dioxane;
2S-[2β,4β(RS),5β]-5-(2'-trifluoromethylbenzyloxy)-4-(1-hydroxypentyl)-2-propyl-1,3-dioxane, etc.

EXAMPLE 15

2S-[2β,4β(RS),5β]-4-(1-benzoyloxyethyl)-5-(2'-chlorobenzyloxy)-2-propyl-1,3-dioxane In this example 1.2 g (0.008 mole) of benzoyl chloride was added dropwise to a solution of 1.5 g (0.005 mole) of 2S-[2β,4β(RS),5β]-5-(2'-chlorobenzyloxy)-4-(1-hydroxyethyl)-2-propyl-1,3-dioxane in 3 ml of pyridine. The reaction mixture was stirred overnight (15 hours) at room temperature and was poured into methylene chloride and water. The organic layer was separated, washed with dilute aqueous hydrochloric acid to remove pyridine, followed by washing with a saturated solution of sodium chloride and dried over anhydrous magnesium sulfate. Concentration by evaporation under reduced pressure afforded the title compound as a liquid.

Similarly, by applying the above procedure to the corresponding compounds illustrated in Example 14, hereinabove, the corresponding benzoyl derivatives can be prepared, for example:

2S-[2β,4β(RS),5β]-5-(2'-fluorobenzloxy)-4-(1-benzoyloxyethyl)-2-propyl-1,3-dioxane;
2S-[2β,4β(RS),5β]-5-(2'-trifluoromethylbenzyloxy)-4-(1-benzoyloxyethyl)-2-propyl-1,3-dioxane;
2S-[2β,4β(RS),5β]-5-(2',6'-dimethylbenzyloxy)-4-(1-benzoyloxyethyl)-2-propyl-1,3-dioxane;
2S-[2β,4β(RS),5β]-5-(2'-methoxybenzyloxy)-4-(1-benzoyloxyethyl)-2-propyl-1,3-dioxane;
2S-[2β,4β(RS),5β]-5-(4'-iodobenzyloxy)-4-(1-benzoyloxyethyl)-2-propyl-1,3-dioxane;
2S-[2β,4β(RS),5β]-5-(3'-propylbenzyloxy)-4-(1-benzoyloxyethyl)-2-propyl-1,3-dioxane;
2S-[2β,4β(RS),5β]-5-[2'-(2,2-dichloroethyl)benzyloxy]-4-(1-benzoyloxyethyl)-2-propyl-1,3-dioxane;
2S-[2β,4β(RS),5β]-5-(3'-chloro-4'-iodobenzyloxy)-4-(1-benzoyloxyethyl)-2-propyl-1,3-dioxane;
2S-[2β,4β(RS),5β]-5-(2',5'-dimethylbenzyloxy)-4-(1-benzoyloxyethyl)-2-propyl-1,3-dioxane;
2S-[2β,4β(RS),5β]-5-(3'-trifluoromethyl-6'-propylbenzyloxy)-4-(1-benzoyloxyethyl)-2-propyl-1,3-dioxane;
2S-[2β,4β(RS),5β]-5-(2'-fluoro-3'-ethylbenzyloxy)-4-(1-benzoyloxyethyl)-2-propyl-1,3-dioxane;
2S-[2β,4β(RS),5β]-5-(2'-iodo-4'-trifluoromethylbenzyloxy)-4-(1-benzoyloxyethyl)-2-propyl-1,3-dioxane;
2S-[2β,4β(RS),5β]-5-(3',5'-dichlorobenzyloxy)-4-(1-benzoyloxyethyl)-2-propyl-1,3-dioxane;
2S-[2β,4β(RS),5β]-2'-chlorobenzyloxy)-4-(1-benzoyloxyethyl)-2-isopropyl-1,3-dioxane;
2S-[2β,4β(RS),5β]-5-(2'-fluorobenzyloxy)-4-(1-benzoyloxyethyl)-2-isopropyl-1,3-dioxane;
2S-[2β,4β(RS),5β]-5-(2'-trifluoromethylbenzyloxy)-4-(1-benzoyloxyethyl)-2-isopropyl-1,3-dioxane;
2S-[2β,4β(RS),5β]-5-(2',6'-dimethylbenzyloxy)-4-(1-benzoyloxyethyl)-2-isopropyl-1,3-dioxane;
2S-[2β,4β(RS),5β]-5-(2'-methoxybenzyloxy)-4-(1-benzoyloxyethyl)-2-isopropyl-1,3-dioxane;
2S-[2β,4β(RS),5β]-5-(4'-iodobenzyloxy)-4-(1-benzoyloxyethyl)-2-isopropyl-1,3-dioxane;
2S-[2β,4β(RS),5β]-5-(3'-propylbenzyloxy)-4-(1-benzoyloxyethyl)-2-isopropyl-1,3-dioxane;
2S-[2β,4β(RS),5β]-5-[2'-(2,2-dichloroethyl)benzyloxy]-4-(1-benzoyloxyethyl)-2-isopropyl-1,3-dioxane;
2S-[2β,4β(RS),5β]-5-(3'-chloro-4'-iodobenzyloxy)-4-(1-benzoyloxyethyl)-2-isopropyl-1,3-dioxane;
2S-[2β,4β(RS),5β]-5-(2',5'-dimethylbenzyloxy)-4-(1-benzoyloxyethyl)-2-isopropyl-1,3-dioxane;
2S-[2β,4β(RS),5β]-5-(3'-trifluoromethyl-6'-propylbenzyloxy)-4-(1-benzoyloxyethyl)-2-isopropyl-1,3-dioxane;
2S-[2β,4β(RS),5β]-5-(2'-fluoro-3'-ethylbenzyloxy)-4-(1-benzoyloxyethyl)-2-isopropyl-1,3-dioxane;
2S-[2β,4β(RS),5β]-5-(2'iodo-'-trifluoromethylbenzyloxy)-4-(1-benzoyloxyethyl)-2-isopropyl-1,3-dioxane;
2S-[2β,4β(RS),5β]-5-(3',5'-dichlorobenzyloxy)-4-(1-benzoyloxyethyl)-2-isopropyl-1,3-dioxane.

Similarly, by applying the above procedure respectively using isobutyrl chloride, 2-methylbutanoyl chloride, hexanoyl chloride, phenoxyacetyl chloride, and 2-chloro-4-trifluoromethylphenoxyoxyacetyl chloride in place of benzoyl chloride, the corresponding isobutyrl, 2-methylbutanoyl, hexanoyl, phenoxyacetyl and 2-chloro-4-trifluoromethylphenoxyacetyl analogs of the above compounds can be prepared, for example:

2S-[2β,4β(RS),5β]-4-(1-isobutyryloxyethyl)-5-(2'-chlorobenzyloxy)-2-propyl-1,3-dioxane;
2S-[2β,4β(RS),5β]-4-[1-(2-methylbutanyl)oxyethyl]5-(2'-chlorobenzyloxy)-2-propyl-1,3-dioxane;
2S-[2β,4β(RS),5β]-4-(1-hexanoyloxyethyl)-5-(2'-chlorobenzyloxy)-2-propyl-1,3-dioxane;
2S-[2β,4β,(RS),5β]-4-(1-phenoxyacetyloxyethyl)-5-(2'-chlorobenzyloxy)-2-propyl-1,3-dioxane; and
2S-[2β,4β(RS),5β]-4-[1-(2'-chloro-4'-trifluoromethylphenoxyacetyl)oxyethyl]-5-(2'-chlorobenzyloxy)-2-propyl-1,3-dioxane; etc.

EXAMPLE 16

2RS-(2α,4α,5α)-Dimethyl 2-(2-chlorophenyl)-1,3-dioxolane-4,5-dicarboxylate

In this example a solution of 200 g (1.12 mole) of (±)-dimethyl tartrate, 166 g (1.18 mol) of 2-chlorobenzaldehyde, and 5 g of p-toluenesulfonic acid in 2 liters of toluene was stirred at reflux temperature for 48 hours, by which time 20.0 ml of water had been azeotropically distilled from the mixture (of a total of 20.2 ml of water theoretically obtainable). The reaction mixture was cooled and washed with a saturated solution of sodium carbonate followed by several portions of saturated sodium chloride solution until the washings were neutral. The organic layer was dried over anhydrous magnesium sulfate, filtered, and evaporated under reduced pressure. The product readily solidified and was collected by filtration and washed with ligroin-ethanol affording 230.2 g (68% yield) of the title compound, mp. 48°-52° C. The product could be further purified by dissolution in a minimum amount of hot ethanol followed by the addition of ligroin (bp 60°-90°) until turbid.

EXAMPLE 17

(±)-3-O-(2-chlorobenzyl)-threitol

In this example 12.0 g (0.315 mole) of lithium aluminum hydride was added portionwise to a solution of 45 g (0.15 mol) of 2RS-(2α,4α,5β)-dimethyl 2-(2-chlorophenyl)-1,3-dioxolane-4,5-dicarboxylate in 1.5 liters of ether-dichloromethane (1:1 by volume) under a nitrogen atmosphere during 0.5 hour. A vigorous exotherm was observed during this process. After the addition was complete, the reacton mixture was stirred another 10 minutes and 22.5 g (0.165 mol) of anhydrous aluminum chloride was added in small portions during 15–20 minutes. The reaction mixture was then refluxed for 4 hours, cooled and treated by successive dropwise addition of 25 ml of water, 25 ml of 10% sodium hydroxide solution, and 25 ml of water. The granular precipitate that separated out was collected by filtration through celite and heated under reflux in 1 liter of ethyl acetate. The hot ethyl acetate extract was then combined with the initial ether-dichloromethane filtrate and concentrated under reduced pressure. Recrystallization by dissolution in a minimum amount of hot ethyl acetate followed by addition of ligroin (bp 60°-90° C.) afforded 30.9 g (84% yield) of the title compound, mp 74°-76° C.

EXAMPLE 18

2RS-(2β,4β,5β)-5-(2-chlorophenyl)methoxy-2-ethyl-4-hydroxymethyl-1,3-dioxane

In this example a mixture of 49.3 g (0.2 mole) of (±)-3-O-(2-chlorobenzyl)-threitol, 24.0 g (0.4 mole) of proprionaldehyde, and 1 g of p-toluenesulfonic acid in 1 liter of toluene was stirred overnight (15–18 hours) at room temperature. The reaction mixture was washed with a dilute sodium hydroxide solution followed by several portions of saturated sodium chloride solution until the washings were neutral. The organic layer was dried over anhydrous magnesium sulfate, filtered, and concentrated under reduced pressure to afford 57.2 g (99% yield) of 2RS-2-ethyl-4-[1-(2-chlorobenzyloxy)-1-hydroxyethyl]-1,3-dioxolane. 20 g of this 1,3-dioxolane derivative was isomerized to the desired 1,3-dioxane by mechanical stirring with 1 g of d,l-camphorsulfonic acid at RT for 2 days. The resulting solidified product was dissolved in 250 ml of dichloromethane and washed with a 5% sodium hydroxide solution followed by several portions of saturated sodium chloride solution until the washings were neutral. The organic layer was dried over anhydrous magnesium sulfate, filtered, and concentrated under reduced pressure. The solidified product was collected by filtration and washed with a small amount of ligroin (bp 60°–90°)-ethanol to afford 14.4 g (72% yield) of the title compound, mp 46°–49° C.

EXAMPLE 19

2RS-(2β,4β,5β)-5-(2-chlorophenyl)methoxy-2-ethyl-1,3-dioxane-4-carboxaldehyde

In this example a solution of 4 ml (0.044 mole) of oxalyl chloride in 100 ml of dichloromethane was stirred at −50° to −60° C. (cooled in dry ice-acetone bath) and 6.8 ml (0.088 mole) of dimethyl sulfoxide in 20 ml of dichloromethane was added slowly with the aid of a syringe. The reaction mixture was then stirred for 2 minutes and 12.0 g (0.041 mol) of 2RS-(2β,4β,5β)-5-(2-chlorophenyl)methoxy-2-ethyl-4-hydroxymethyl-1,3-dioxane in 40 ml of dichloromethane was added dropwise within 10 minutes. After the reaction mixture was stirred an additional 1.5 hours at −50° to −60° C., 28 ml of triethylamine was added slowly and the reaction miture was allowed to warm to room temperature. The solution was treated with dichloromethane and washed successively with water, dilute hydrochloric acid solution, and a saturated sodium chloride solution. The organic layer was dried over anhydrous magnesium sulfate, filtered, and evaporated under reduced pressure to afford 10.4 g (87% yield) of the title compound as a chromatographically homogeneous liquid.

EXAMPLE 20

2RS-(2β,4β,5β)-5-(2-chlorophenyl)methoxy-2-ethyl-4-(1-hydroxyethyl)-1,3-dioxane

In this example 30 ml (0.08 mol) of methyl magnesium bromide (2.85M in anhydrous diethyl ether) was added to 5.7 g (0.02 mol) of 2RS-[2β, 4β,5β]-5-(2-chlorophenyl)methoxy-2-ethyl-1,3-dioxane-4-carboxaldehyde in 50 ml of diethyl ether and the resulting reaction mixture was refluxed for 1 hour. After cooling, the reaction mixture was added to a 25% aqueous ammonium chloride solution. Diethyl ether was added and the diethyl ether phase was separated, washed with saturated sodium chloride solution, dried over anhydrous magnesium sulfate and evaporated under reduced pressure to afford after recrystallization from ethanol-ligroin (bp 60°–90° C.) 3.8 g (63% yield) of the title compound as the epimeric alcohols, mp 64°–72° C.

EXAMPLE 21

2RS-(2β,4β,5β)-5-(2-chlorophenyl)methoxy-2-ethyl-4-(1-hydroxypropyl)-1,3-dioxane In this example 50 ml (0.14 mole) of ethyl magnesium bromide (2.85M in anhydrous diethyl ether) was added to 8.3 g (0.029 mol) of 2RS-(2β,4β,5β)-5-(2-chlorophenyl)methoxy-2-ethyl-1,3-dioxane-4-carboxaldehyde in 100 ml of diethyl ether and the resulting reaction mixture was refluxed for 1 hour. After workup as described above, 8.3 g (90% yield) of the title compound as the epimeric alcohols was obtained.

EXAMPLE 22

2RS-(2β,4β,5β)-4-acetyl-5-(2-chlorophenyl)methoxy-2-ethyl-1,3-dioxane

In this example 1.7 g (16 mmole) of chromium trioxide ($CrO_3$) dissolved in 15 ml of water-acetic acid (1:4 by volume) was added dropwise to an ice-cooled solution of 2.5 g (8.2 mmol) of 2RS-(2β,4β,5β)-5-(2-chlorophenyl)methoxy-2-ethyl-4-(α-hydroxyethyl)-1,3-dioxane dissolved in 10 ml of glacial acetic acid and stirred 2 hours at room temperature. The reaction mixture was then diluted with water and dichloromethane and the organic extract was washed with a dilute sodium carbonate solution followed by several portions of saturated sodium chloride solution until the washings were neutral. The organic layer was dried over anhydrous magnesium sulfate, filtered, and concentrated under reduced pressure. The product was subsequently further purified by flash column chromatography (2.5×30 cm of silica gel) eluting with dichloromethane to afford 1.4 g (56% yield) of the title compound as a colorless liquid.

EXAMPLE 23

Similarly, by applying the procedures of Examples 16—22, using the appropriate starting materials, the corresponding 2RS racemic mixtures of the 2S products illustrated in the above examples can be prepared. The 2RS $R^3$ acyl derivatives can be prepared via the procedure described in Example 15 using the appropriate acyl chloride or bromide.

EXAMPLE 24

The compounds listed in Table A hereinbelow were prepared using the appropriate materials and the appropriate procedures described in the Examples hereinabove.

TABLE A

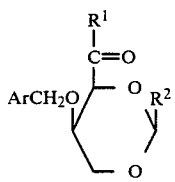

| No. | Isomer | $R^1$ | $R^2$ | Ar | Carbon Calc. | Carbon Found | Hydrogen Calc. | Hydrogen Found | Melting Point °C. |
|---|---|---|---|---|---|---|---|---|---|
| 1 | S* | $CH_3$ | $CH_3$ | 2-Cl$\phi$*** | 59.06 | 57.95 | 6.02 | 6.26 | Liq. |
| 2 | S | $CH_3$ | $C_2H_5$ | 2-Cl$\phi$ | 60.30 | 59.80 | 6.41 | 6.56 | Liq. |
| 3 | S | $CH_3$ | $(CH_2)_2CH_3$ | 2-Cl$\phi$ | 61.44 | 60.55 | 6.77 | 6.79 | Liq. |
| 4 | S | $CH_3$ | $CH(CH_3)_2$ | 2-Cl$\phi$ | 61.44 | 61.27 | 6.77 | 6.86 | Liq. |
| 5 | S | $CH_3$ | $C_2H_5$ | 2-$CH_3\phi$ | 69.04 | 69.04 | 7.97 | 7.99 | 40-41 |
| 6 | S | $CH_3$ | $(CH_2)_2CH_3$ | 2-$CH_3\phi$ | 69.84 | 69.21 | 8.27 | 8.77 | 34-36 |
| 7 | RS** | $CH_3$ | $(CH_2)_2CH_3$ | 2-Cl$\phi$ | 61.44 | 61.66 | 6.77 | 6.82 | Liq. |
| 8 | RS | $C_2H_5$ | $(CH_2)_2CH_3$ | 2-Cl$\phi$ | 62.48 | 62.04 | 7.09 | 7.35 | Liq. |
| 9 | RS | $C_2H_5$ | $C_2H_5$ | 2-Cl$\phi$ | 61.44 | 61.05 | 6.77 | 6.61 | Liq. |
| 10 | RS | $CH_3$ | $C_2H_5$ | 2-Cl$\phi$ | 60.30 | 59.74 | 6.41 | 7.00 | Liq. |
| 11 | RS | $CH_3$ | $C_2H_5$ | 2-$CH_3\phi$ | 69.04 | 69.35 | 7.97 | 8.30 | Liq. |
| 12 | RS | $C_2H_5$ | $C_2H_5$ | 2-$CH_3\phi$ | 69.84 | 69.53 | 8.27 | 8.63 | Liq. |

*S = 2S—(2β,4β,5β)
**RS = Racemic mixture of 2S—[2β,4β,5β]- and 2R—[2β,4β,5β]-
***$\phi$ = Phenyl, for example, 2-Cl$\phi$ = 2-chlorophenyl

TABLE B-1

| No. | Isomer | $R^1$ | $R^2$ | Ar | Carbon Calc. | Carbon Found | Hydrogen Calc. | Hydrogen Found | Melting Point °C. |
|---|---|---|---|---|---|---|---|---|---|
| 13 | S'*1 | $CH_3$ | $CH_3$ | 2-Cl$\phi$ | 58.64 | 58.51 | 6.68 | 6.92 | 43-45 |
| 14 | S' | $CH_3$ | $C_2H_5$ | 2-Cl$\phi$ | 59.90 | 59.50 | 7.04 | 7.17 | 81-83 |
| 15 | S' | $CH_3$ | $(CH_2)_2CH_3$ | 2-Cl$\phi$ | 61.05 | 60.46 | 7.36 | 7.47 | 80-82 |
| 16 | S' | $CH_3$ | $CH_2(CH_3)_2$ | 2-Cl$\phi$ | 61.05 | 61.58 | 7.36 | 7.54 | 110-113 |
| 17 | S' | $CH_3$ | $C_2H_5$ | 2-$CH_3\phi$ | 68.54 | 67.92 | 8.63 | 8.90 | 65-67 |
| 18 | S' | $CH_3$ | $(CH_2)_2CH_3$ | 2-$CH_3\phi$ | 69.36 | 69.65 | 8.90 | 9.75 | 82-85 |
| 19 | S' | $CH_3$ | $CH_2(CH_3)_2$ | 2-$CH_3\phi$ | 69.36 | 69.26 | 8.90 | 9.68 | 88-92 |
| 20 | S' | $CH_3$ | $C_2H_5$ | 2-F$\phi$ | 63.37 | 65.63 | 7.44 | 7.79 | 79-82 |
| 21 | S' | $CH_3$ | $(CH_2)_2CH_3$ | 2-F$\phi$ | 64.41 | 67.19 | 7.77 | 8.30 | 87-89 |
| 22 | RS*2 | $CH_3$ | $(CH_2)_2CH_3$ | 2-Cl$\phi$ | 61.05 | 61.21 | 7.36 | 7.80 | 44-48 |
| 23 | RS | $C_2H_5$ | $C_2H_5$ | 2-Cl$\phi$ | 61.05 | 59.06 | 7.36 | 7.27 | Liq. |
| 24 | RS | $C_2H_5$ | $(CH_2)_2CH_3$ | 2-Cl$\phi$ | 62.09 | 59.54 | 7.66 | 7.65 | Liq. |
| 25 | RS | $CH_3$ | $C_2H_5$ | 2-Cl$\phi$ | 59.90 | 60.00 | 7.04 | 7.91 | 64-72 |

*1S' = 2S—[2β,4β(S),5β]—
*2RS = Racemic mixture of 2S—[2β,4β(RS),5β]— and 2R—[2β,4β(RS),5β]—

TABLE B-2

| No. | Isomer | $R^1$ | $R^2$ | Ar | Y | Carbon Calc. | Carbon Found | Hydrogen Calc. | Hydrogen Found | Melting Point °C. |
|---|---|---|---|---|---|---|---|---|---|---|
| 26 | S'*1 | $CH_3$ | $(CH_2)_2CH_3$ | 2-Cl$\phi$** | $CH_3$ | 60.59 | 60.90 | 7.06 | 7.29 | 50-52 |
| 27 | S' | $CH_3$ | $(CH_2)_2CH_3$ | 2-Cl$\phi$ | $(CH_2)_2CH_3$ | 62.41 | 61.98 | 7.59 | 7.72 | Liq. |
| 28 | S' | $CH_3$ | $CH_3$ | 2-Cl$\phi$ | $\phi$ | 64.53 | 65.62 | 5.93 | 6.30 | Liq. |
| 29 | S' | $CH_3$ | $C_2H_5$ | 2-Cl$\phi$ | $\phi$ | 65.26 | 65.37 | 6.22 | 6.59 | 50-52 |
| 30 | S' | $CH_3$ | $(CH_2)_2CH_3$ | 2-Cl$\phi$ | $\phi$ | 65.94 | 62.58 | 6.50 | 6.59 | 53-55 |
| 31 | S' | $CH_3$ | $CH_2(CH_3)_2$ | 2-Cl$\phi$ | $\phi$ | 65.94 | 65.64 | 6.50 | 6.77 | 76-78 |
| 32 | S' | $CH_3$ | $(CH_2)_2CH_3$ | 2-Cl$\phi$ | 2-Cl$\phi$ | 60.93 | 60.00 | 5.78 | 5.54 | Liq. |
| 33 | S' | $CH_3$ | $(CH_2)_2CH_3$ | 2-Cl$\phi$ | 4-Cl$\phi$ | 60.93 | 60.71 | 5.78 | 5.23 | 75-80 |
| 34 | S' | $CH_3$ | $(CH_2)_2H_3$ | 2-Cl$\phi$ | 2,4-diCl—$\phi$OCH_2 | 55.67 | 56.96 | 5.26 | 5.15 | 63-70 |

TABLE B-2-continued

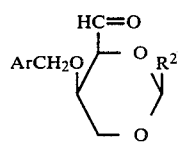

| No. | Isomer | R¹ | R² | Ar | Y | ELEMENTAL ANALYSIS | | | | Melting Point °C. |
|-----|--------|----|----|----|----|---|---|---|---|---|
| | | | | | | Carbon | | Hydrogen | | |
| | | | | | | Calc. | Found | Calc. | Found | |
| 35 | S' | $CH_3$ | $C_2H_5$ | 2-$CH_3\phi$ | $\phi$ | 71.85 | 72.41 | 7.34 | 7.92 | 89–91 |
| 36 | S' | $CH_3$ | $(CH_2)_2CH_3$ | 2-$CH_3\phi$ | $\phi$ | 72.34 | 71.39 | 7.59 | 8.00 | 88–91 |
| 37 | S' | $CH_3$ | $CH(CH_3)_2$ | 2-$CH_3\phi$ | $\phi$ | 72.34 | 72.25 | 7.59 | 8.17 | 92–95 |
| 38 | S' | $CH_3$ | $C_2H_5$ | 2-$CH_3\phi$ | 2,4-diCl—$\phi OCH_2$ | 59.63 | 59.22 | 5.84 | 5.53 | 80–87 |
| 39 | S' | $CH_3$ | $C_2H_5$ | 2-F$\phi$ | $\phi$ | 68.03 | 72.27 | 6.49 | 7.00 | 49–53 |
| 40 | S' | $CH_3$ | $(CH_2)_2CH_3$ | 2-F$\phi$ | $\phi$ | 68.64 | 72.75 | 6.76 | 7.32 | 53–55 |
| 41 | S(RS)* | $CH_3$ | $(CH_2)_2CH_3$ | 2-Cl$\phi$ | $\phi$ | 65.94 | 64.52 | 6.50 | 6.62 | Liq. |

*¹S' = 2S—[2β,4β(S),5β]—
*S(RS) = 2S—[2β,4β(RS),5β]—
**φ = phenyl

TABLE C
COMPARISON COMPOUNDS

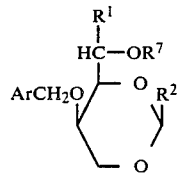

| No. | (Isomer) | R² | Ar | ELEMENTAL ANALYSIS | | | | Melting Point °C. |
|-----|----------|----|----|---|---|---|---|---|
| | | | | Carbon | | Hydrogen | | |
| | | | | Calc. | Found | Calc. | Found | |
| C-1 | S* | $(CH_2)_2CH_3$ | 2-Cl$\phi$*** | 60.30 | 58.64 | 6.41 | 7.06 | Liq. |
| C-2 | RS** | $C_2H_5$ | 2-Cl$\phi$ | 59.06 | 56.16 | 6.02 | 6.16 | Liq. |
| C-3 | RS | $(CH_2)_2CH_3$ | 2-Cl$\phi$ | 60.30 | 59.63 | 6.41 | 6.63 | Liq. |

*S = 2S—(2β,4β,5β)
**RS = Racemic mixture of 2S—(2β,4β,5β)- and 2R—(2β,4β,5β)-
***φ = Phenyl

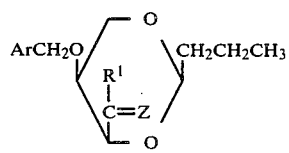

| No. | (Isomer) | R¹ | R² | R⁷ | Ar | ELEMENTAL ANALYSIS | | | | Melting Point °C. |
|-----|----------|----|----|----|----|---|---|---|---|---|
| | | | | | | Carbon | | Hydrogen | | |
| | | | | | | Calc. | Found | Calc. | Found | |
| C-4 | S'*¹ | H | $C_2H_5$ | H | 2-Cl$\phi$ | 58.64 | 58.75 | 6.68 | 6.69 | 48–52 |
| C-5 | S' | H | $(CH_2)_2CH_3$ | H | 2-Cl$\phi$ | 59.89 | 60.65 | 7.04 | 7.41 | 75.0 |
| C-6 | S' | H | $(CH_2)_2CH_3$ | $CH_3$ | 2-Cl$\phi$ | 61.05 | 63.34 | 7.36 | 7.88 | Liq. |
| C-7 | S' | $CH_3$ | $(CH_2)_2CH_3$ | $CH_3$ | 2-Cl$\phi$ | 62.09 | 62.94 | 7.66 | 7.85 | Liq. |
| C-8 | S' | $CH_3$ | $C_2H_5$ | benzyl | 2-Cl$\phi$ | 67.60 | 69.18 | 6.96 | 7.22 | Liq. |
| C-9 | S' | H | $(CH_2)_2CH_3$ | benzoyl | 2-Cl$\phi$ | 65.26 | 68.43 | 6.22 | 6.71 | 55–58 |
| C-10 | S' | H | $C_2H_5$ | benzoyl | 2-Cl$\phi$ | 64.53 | 65.00 | 5.93 | 6.17 | Liq. |

*¹S¹ = 2S—[2β,4β(S),5β]-

| No. | (Isomer) | R¹ | Z | Ar | ELEMENTAL ANALYSIS | | | | Melting Point °C. |
|-----|----------|----|---|----|---|---|---|---|---|
| | | | | | Carbon | | Hydrogen | | |
| | | | | | Calc. | Found | Calc. | Found | |
| C-11 | R* | $CH_3$ | =O | 2-Cl$\phi$ | 61.44 | 58.30 | 6.77 | 6.88 | Liq. |

*R = 2R—(2β,4β,5β)

TABLE C-continued

COMPARISON COMPOUNDS

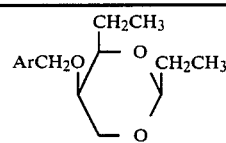

| No. | (Isomer) | Ar | Carbon Calc. | Carbon Found | Hydrogen Calc. | Hydrogen Found | Melting Point °C. |
|---|---|---|---|---|---|---|---|
| C-12 | RS** | 2-Clφ | 63.26 | 60.61 | 7.43 | 7.15 | Liq. |

RS** = racemic mixture 2S—[2β,4β,5β]- and 2R—[2β,4β,5β]-

EXAMPLE 25

In this example, the compounds of Example 24 were respectively tested using the procedures described hereinbelow for pre-emergent and post-emergent activity against a variety of grasses and broad-leaf plants including one grain crop and one broad-leaf crop. The compounds tested are identified by compound number in Table A hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm² or in some instances as indicated in Table 1 hereinbelow, certain of the compounds were tested at a lower dosage of 15.6 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Watergrass | Crabgrass | Wild Oats | Rice |
| 1 | 70 | 80 | 85 | 80 | 100 | 100 | 100 | 100 |
| 2 | 80 | 90 | 80 | 90 | 100 | 100 | 100 | 100 |
| 3 | 60 | 80 | 70 | 30 | 100 | 100 | 100 | 100 |
| 4 | 65 | 70 | 65 | 25 | 100 | 100 | 100 | 100 |
| 5 | 75 | 70 | 70 | 65 | 100 | 100 | 100 | 100 |
| 6 | 70 | 70 | 55 | 45 | 100 | 100 | 100 | 100 |
| 7* | 70 | 70 | 65 | 0 | 100 | 100 | 100 | 100 |
| 8* | 55 | 55 | 55 | 75 | 100 | 100 | 100 | 100 |
| 9* | 65 | 70 | 65 | 90 | 100 | 100 | 99 | 100 |
| 10* | 45 | 45 | 45 | 60 | 100 | 100 | 100 | 100 |
| 11* | 75 | 75 | 70 | 70 | 100 | 100 | 100 | 100 |
| 12* | 80 | 70 | 60 | 75 | 100 | 100 | 100 | 100 |
| 13 | 65 | 80 | 80 | 75 | 100 | 100 | 100 | 100 |
| 14 | 80 | 80 | 70 | 80 | 100 | 100 | 100 | 100 |
| 15 | 70 | 80 | 75 | 45 | 100 | 100 | 100 | 98 |
| 16 | 70 | 75 | 75 | 20 | 100 | 100 | 100 | 100 |
| 17 | 85 | 80 | 90 | 75 | 100 | 100 | 100 | 100 |
| 18 | 90 | 85 | 90 | 60 | 100 | 100 | 100 | 100 |
| 19 | 70 | 70 | 80 | 70 | 100 | 100 | 100 | 100 |
| 20 | 90 | 80 | 90 | 90 | 100 | 100 | 100 | 100 |
| 21 | 85 | 80 | 90 | 70 | 100 | 100 | 100 | 100 |
| 22 | 75 | 70 | 65 | 0 | 100 | 100 | 93 | 95 |
| 23 | 70 | 70 | 55 | 75 | 100 | 100 | 95 | 95 |
| 24 | 55 | 40 | 35 | 35 | 100 | 100 | 90 | 95 |

TABLE 1-continued

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Watergrass | Crabgrass | Wild Oats | Rice |
| 25 | 55 | 55 | 45 | 70 | 100 | 100 | 90 | 100 |
| 26 | 67 | 82 | 92 | 32 | 100 | 100 | 100 | 97 |
| 27 | 75 | 80 | 92 | 32 | 100 | 100 | 100 | 95 |
| 28 | 60 | 80 | 80 | 70 | 100 | 100 | 90 | 98 |
| 29 | 80 | 80 | 80 | 90 | 100 | 100 | 100 | 100 |
| 30 | 65 | 75 | 70 | 35 | 100 | 100 | 85 | 95 |
| 31 | 35 | 40 | 35 | 20 | 98 | 100 | 75 | 70 |
| 32 | 0 | 0 | 0 | 0 | 80 | 70 | 0 | 0 |
| 33 | 0 | 0 | 0 | 0 | 80 | 75 | 0 | 10 |
| 34 | 99 | 99 | 99 | 65 | 100 | 100 | 93 | 95 |
| 35 | 15 | 55 | 55 | 85 | 100 | 100 | 90 | 100 |
| 36 | 50 | 50 | 55 | 65 | 100 | 100 | 85 | 100 |
| 37 | 50 | 50 | 55 | 60 | 100 | 100 | 93 | 100 |
| 38 | 100 | 100 | 100 | 75 | 100 | 100 | 90 | 95 |
| 39 | 90 | 90 | 95 | 93 | 100 | 100 | 100 | 100 |
| 40 | 85 | 80 | 95 | 60 | 100 | 100 | 100 | 100 |
| 41 | 75 | 75 | 65 | 10 | 100 | 100 | 85 | 98 |

*contains 10% 2,6-di-t-butyl-4-methylphenol by weight as an antioxidant

TABLE 1A

COMPARISON COMPOUNDS
Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Watergrass | Crabgrass | Wild Oats | Rice |
| C-1 | 10 | 10 | 0 | 25 | 15 | 10 | 20 | 0 |
| C-2 | 0 | 0 | 0 | 0 | 0 | 0 | 0 | 0 |
| C-3 | 0 | 0 | 0 | 20 | 25 | 25 | 0 | 0 |
| C-4 | 25 | 30 | 15 | 20 | 55 | 68 | 10 | 75 |
| C-5 | 0 | 63 | 50 | 62 | 55 | 35 | 30 | 92 |
| C-6 | 50 | 40 | 65 | 60 | 100 | 100 | 90 | 100 |
| C-7 | 25 | 10 | 25 | 0 | 85 | 90 | 40 | 65 |
| C-8 | 55 | 25 | 30 | 15 | 100 | 100 | 50 | 80 |
| C-9 | 0 | 0 | 0 | 50 | 40 | 60 | 0 | 0 |
| C-10 | 0 | 0 | 0 | 0 | 50 | 55 | 20 | 35 |
| C-11 | 0 | 0 | 0 | 0 | 0 | 0 | 0 | 0 |
| C-12 | 75 | 70 | 70 | 85 | 100 | 100 | 100 | 100 |

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Watergrass | Crabgrass | Wild Oats | Rice |
| 1 | 55 | 50 | 35 | 50 | 65 | 98 | 65 | 60 |
| 2 | 30 | 50 | 50 | 40 | 100 | 50 | 70 | 80 |
| 3 | 30 | 30 | 20 | 20 | 100 | 30 | 90 | 30 |
| 4 | 0 | 0 | 0 | 25 | 85 | 45 | 45 | 30 |
| 5 | 20 | 20 | 20 | 25 | 100 | 75 | 70 | 70 |
| 6 | 30 | 30 | 30 | 25 | 75 | 65 | 45 | 45 |
| 7* | 10 | 25 | 30 | 25 | 90 | 55 | 45 | 50 |
| 8* | 20 | 25 | 20 | 45 | 45 | 30 | 10 | 10 |
| 9* | 20 | 25 | 20 | 50 | 60 | 40 | 25 | 25 |
| 10* | 20 | 30 | 25 | 35 | 65 | 65 | 50 | 35 |
| 11* | 45 | 50 | 40 | 50 | 75 | 55 | 55 | 50 |
| 12* | 35 | 40 | 40 | 70 | 40 | 55 | 45 | 50 |
| 13 | 50 | 60 | 50 | 45 | 60 | 65 | 35 | 45 |
| 14 | 30 | 30 | 30 | 40 | 100 | 60 | 60 | 60 |
| 15 | 30 | 30 | 30 | 20 | 100 | 40 | 70 | 20 |
| 16 | 0 | 0 | 0 | 0 | 80 | 60 | 35 | 35 |
| 17 | 25 | 25 | 25 | 30 | 90 | 70 | 60 | 65 |
| 18 | 20 | 30 | 25 | 25 | 75 | 70 | 70 | 65 |
| 19 | 0 | 0 | 0 | 0 | 85 | 70 | 70 | 60 |
| 20 | 80 | 80 | 80 | 65 | 93 | 75 | 70 | 50 |
| 21 | 20 | 25 | 30 | 20 | 100 | 75 | 55 | 55 |
| 22 | 0 | 20 | 0 | 25 | 80 | 40 | 45 | 45 |
| 23 | 0 | 0 | 0 | 40 | 40 | 20 | 0 | 0 |
| 24 | 0 | 0 | 0 | 0 | 15 | 0 | 0 | 0 |
| 25 | 25 | 25 | 25 | 30 | 95 | 65 | 35 | 30 |

TABLE 2-continued

Post-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Watergrass | Crabgrass | Wild Oats | Rice |
| 26 | 50 | 68 | 55 | 30 | 98 | 72 | 72 | 65 |
| 27 | 50 | 35 | 0 | 0 | 85 | 68 | 57 | 55 |
| 28 | 25 | 30 | 50 | 35 | 30 | 65 | 0 | 0 |
| 29 | 30 | 30 | 30 | 30 | 100 | 50 | 60 | 70 |
| 30 | 50 | 0 | 30 | 0 | 0 | 0 | 0 | 0 |
| 31 | 0 | 0 | 0 | 0 | 70 | 35 | 35 | 20 |
| 32 | 0 | 0 | 0 | 0 | 0 | 0 | 0 | 0 |
| 33 | 0 | 0 | 0 | 0 | 0 | 0 | 0 | 0 |
| 34 | 90 | 90 | 75 | 90 | 0 | 0 | 0 | 0 |
| 35 | 25 | 30 | 20 | 20 | 95 | 75 | 80 | 65 |
| 36 | 20 | 25 | 20 | 0 | 90 | 70 | 75 | 45 |
| 37 | 0 | 0 | 0 | 0 | 75 | 70 | 70 | 25 |
| 38 | 85 | 95 | 85 | 85 | 75 | 45 | 70 | 20 |
| 39 | 0 | 0 | 30 | 0 | 70 | 100 | 90 | 75 |
| 40 | 0 | 0 | 0 | 0 | 80 | 100 | 80 | 75 |
| 41 | 20 | 25 | 25 | 10 | 65 | 35 | 35 | 10 |

*contains 10% 2,6-di-t-butyl-4-methylphenol by weight as an antioxidant

TABLE 2A

COMPARISON COMPOUNDS
Post-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Watergrass | Crabgrass | Wild Oats | Rice |
| C-1 | 0 | 0 | 0 | 0 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 40 | 30 | 0 | 25 | 0 | 0 | 0 | 0 |
| C-6 | 25 | 25 | 25 | 45 | 10 | 15 | 10 | 10 |
| C-7 | 0 | 0 | 0 | 0 | 0 | 0 | 0 | 0 |
| C-8 | 15 | 50 | 15 | 15 | 70 | 35 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 0 | 0 | 0 | 0 |
| C-12 | 35 | 40 | 30 | 40 | 85 | 50 | 60 | 25 |

As can be seen from the above Tables, the compounds of the invention generally exhibit both pre-emergence and post-emergence activity. The compounds generally exhibit excellent pre-emergence activity against grasses and especially so Compounds Nos. 2, 3, 5, 6, 14, 15 and 29. In contrast to this, with the exception of Compounds C-6, C-8 and C-12 which exhibited very good pre-emergence grass phytotoxicity (Table 1-A), the comparison compounds were generally inactive or exhibited substantially poorer activity than the corresponding isomers or nearest analogs of the present invention. For example, it can be seen that, whereas Compound 3 was very active, its 2R isomer, i.e. Compound C-11, was wholly inactive.

EXAMPLE 26

The compounds listed by compound number in the following table were tested for pre-emergence herbicidal activity at low dosage application rates of 4.4; 1.8; 0.7 and 0.28 micrograms/cm$^2$. The results of this testing is given in Table 3 hereinbelow, wherein the Compound Numbers refer to the compound numbers assigned the respective compounds in Example 24 hereinabove. This testing was conducted in the same manner as described in Example 25, with the exception, that the application rates given in Table 3 were used and that the number of plant pots per compound per dosage ratio was increased to four.

TABLE 3

Pre-Emergence Herbicidal Activity
Low Dosage Tests

| Compound No. | Dosage γ/cm$^2$* | Broad-Leaf Plants % Phytotoxicity | | | | Grasses % Phytotoxicity | | | |
|---|---|---|---|---|---|---|---|---|---|
| | | Lambsquarter | Mustard | Pigweed | Soybean | Watergrass | Crabgrass | Wild Oats | Rice |
| 2 | 4.4 | 72 | 90 | 62 | 43 | 100 | 100 | 100 | 100 |
| 2 | 1.8 | 70 | 83 | 60 | 7 | 100 | 100 | 94 | 99 |
| 2 | 0.7 | 70 | 75 | 60 | 0 | 100 | 100 | 82 | 87 |
| 2 | 0.28 | 60 | 33 | 48 | 0 | 100 | 100 | 75 | 67 |
| 3 | 4.4 | 92 | 82 | 63 | 2 | 100 | 100 | 95 | 98 |
| 3 | 1.8 | 88 | 53 | 37 | 2 | 100 | 100 | 82 | 100 |
| 3 | 0.7 | 17 | 0 | 35 | 0 | 100 | 97 | 65 | 80 |
| 3 | 0.28 | 0 | 0 | 33 | 0 | 93 | 89 | 42 | 57 |

TABLE 3-continued

| | | Pre-Emergence Herbicidal Activity Low Dosage Tests | | | | | | | |
|---|---|---|---|---|---|---|---|---|---|
| | | Broad-Leaf Plants % Phytotoxicity | | | | Grasses % Phytotoxicity | | | |
| Compound No. | Dosage γ/cm²* | Lambs-quarter | Mustard | Pigweed | Soybean | Watergrass | Crabgrass | Wild Oats | Rice |
| 15 | 4.4 | 95 | 72 | 82 | 13 | 100 | 100 | 98 | 95 |
| 15 | 1.8 | 93 | 37 | 100 | 7 | 100 | 100 | 88 | 93 |
| 15 | 0.7 | 60 | 0 | 37 | 3 | 99 | 97 | 62 | 65 |
| 15 | 0.28 | 30 | 0 | 37 | 0 | 92 | 70 | 40 | 45 |
| C-6 | 4.4 | 62 | 0 | 40 | 10 | 99 | 98 | 30 | 53 |
| C-6 | 1.8 | 20 | 0 | 20 | 0 | 75 | 20 | 0 | 7 |
| C-6 | .7 | 13 | 0 | 10 | 0 | 20 | 0 | 0 | 0 |
| C-6 | 0.28 | 0 | 0 | 0 | 0 | 0 | 0 | 0 | 0 |
| 29 | 4.4 | 88 | 83 | 99 | 23 | 100 | 100 | 93 | 97 |
| 29 | 1.8 | 83 | 72 | 98 | 13 | 100 | 100 | 90 | 87 |
| 29 | 0.7 | 73 | 40 | 98 | 5 | 98 | 100 | 85 | 73 |
| 29 | 0.28 | 53 | 20 | 87 | 0 | 93 | 93 | 52 | 53 |
| C-8 | 4.4 | 57 | 40 | 40 | 0 | 80 | 94 | 20 | 22 |
| C-8 | 1.8 | 30 | 27 | 20 | 0 | 58 | 45 | 0 | 0 |
| C-8 | 0.7 | 27 | 0 | 7 | 0 | 30 | 12 | 0 | 0 |
| C-8 | 0.28 | 0 | 0 | 0 | 0 | 10 | 0 | 0 | 0 |

*γ/cm² = Micrograms per square centimeter

Obviously, many modifications and variations of the invention described hereinabove and below can be made without departing from the essence and scope thereof.

What is claimed is:

1. A compound having the formula:

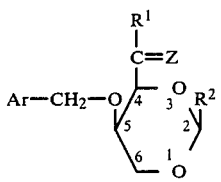 (I)

wherein
R¹ is methyl, ethyl, n-propyl or n-butyl;
R² is lower alkyl having 1 through 6 carbon atoms;
Ar is phenyl, thienyl, pyridyl or substituted phenyl having 1 or 2 substituents independently selected from the group of lower alkyl having 1 through 6 carbon atoms; lower alkoxy having 1 through 6 carbon atoms; halo; and haloalkyl having 1 or 2 carbon atoms and 1 through 4 of the same or different halo atoms; and
Z is oxo or the group

wherein the wavy bond line indicates that the carbon atom to which the OR³ group is attached can be R or S oriented, and R³ is hydrogen, lower alkanoyl having 2 through 6 carbon atoms, benzoyl, phenoxyacetyl or substituted phenoxyacetyl having one or two substituents on the phenyl ring independently selected from the group of fluoro, chloro, bromo, iodo or trifluoromethyl;
and wherein said compound of Formula I has the stereo configuration 2-S-(2β,4β,5β)-.

2. The compound of claim 1 wherein R² is methyl, ethyl, isopropyl or n-propyl.

3. The compound of claim 1 wherein Ar is phenyl or said substituted phenyl.

4. The compound of claim 1 wherein Ar is phenyl or a monosubstituted phenyl having its sole substituent at the 2-position of the phenyl ring.

5. The compound of claim 1 wherein Ar is 2-halophenyl or 2-trifluoromethylphenyl.

6. The compound of claim 1 wherein Ar is 2-chlorophenyl.

7. The compound of claim 1 wherein Ar is thienyl or pyridyl.

8. The compound of claim 1 wherein Ar is 2,6-dimethylphenyl.

9. The compound of claim 1 wherein R¹ is methyl or ethyl.

10. A compound having the formula:

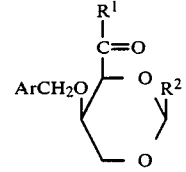

wherein R¹ is methyl, ethyl, n-propyl or n-butyl; R² is lower alkyl having 1 through 6 carbon atoms; Ar is phenyl, thienyl, pyridyl or substituted phenyl having 1 or 2 substituents independently selected from the group of lower alkyl having 1 through 6 carbon atoms; lower alkoxy having 1 through 6 carbon atoms; halo; and haloalkyl having 1 or 2 carbon atoms and 1 through 4 of the same or different halo atoms; and wherein said compound has the stereo configuration 2-S-(2beta,4beta,5-beta).

11. The compound of claim 10 wherein R¹ is methyl or ethyl and R² is methyl, ethyl, isopropyl or n-propyl.

12. The compound of claim 11 wherein Ar is phenyl 2-halophenyl, 2-trifluoromethylphenyl, 2-methylphenyl or 2,6-dimethylphenyl.

13. The compound of claim 12 wherein Ar is 2-chlorophenyl or 2-methylphenyl, R¹ is methyl and R² is ethyl or n-propyl.

14. The compound of claim 13 wherein Ar is 2-chlorophenyl and R² is ethyl.

15. The compound of claim 13 wherein Ar is 2-methylphenyl and R² is ethyl.

16. The compound of claim 1 wherein said compound is selected from the group having the formula:

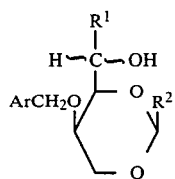

wherein $R^1$, $R^2$, Ar and the wavy bond line are as defined in claim 1.

17. The compound of claim 16 wherein said compound has the stereo configuration 2S-[2β,4β(S),5β].

18. The compound of claim 16 wherein $R^1$ is methyl or ethyl; $R^2$ is methyl, ethyl, isopropyl or n-propyl.

19. The compound of claim 18 wherein Ar is phenyl, 2-halophenyl, 2-trifluoromethylphenyl, 2-methylphenyl or 2,6-dimethylphenyl.

20. The compound of claim 19 wherein Ar is 2-chlorophenyl, $R^1$ is methyl and $R^2$ is ethyl.

21. The compound of claim 19 wherein Ar is 2-chlorophenyl, $R^1$ is methyl and $R^2$ is n-propyl.

22. The compound of claim 1 wherein said compound is selected from the group having the formula:

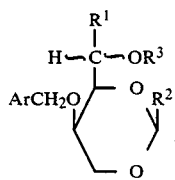

wherein $R^1$, $R^2$, $R^3$ Ar and the wavy bond lines are as defined in claim 1.

23. The compound of claim 22 wherein $R^1$ is methyl or ethyl and $R^2$ is methyl, ethyl, isopropyl or n-propyl.

24. The compound of claim 23 wherein Ar is phenyl, 2-halophenyl, 2-trifluoromethylphenyl, 2-methylphenyl or 2,6-dimethylphenyl.

25. The compound of claim 22 wherein $R^3$ is benzoyl or 2′,4′-dichlorophenoxyacetyl.

26. The compound of claim 25 wherein $R^1$ is methyl and $R^2$ is ethyl or n-propyl and Ar is 2-chlorophenyl.

27. The compound of claim 24 wherein $R^2$ is ethyl.

28. The compound of claim 1 wherein $R^1$ is methyl, $R^2$ is ethyl, Ar is 2-chlorophenyl or 2-methylphenyl and Z is oxo or the group

wherein $R^3$ is hydrogen or benzoyl.

29. The compound of claim 1 wherein Ar is 2-fluorophenyl.

30. The compound of claim 1 wherein Ar is 2-methylphenyl.

31. A composition comprising a compound according to claim 1 in mixture with its corresponding isomer having the formula:

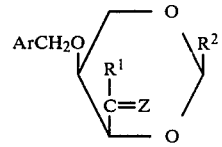

wherein $R^1$, $R^2$, Ar and Z are as defined in claim 1.

32. The composition of claim 31 wherein said mixture is a racemic mixture.

33. A herbicidal composition comprising a herbicidally effective amount of a compound according to claim 1, or mixtures of such compounds, and a compatible carrier.

34. A herbicidal composition comprising a herbicidally effective amount of a compound according to claim 28, or mixtures thereof, and a compatible carrier.

35. A herbicidal composition comprising a herbicidally effective amount of a compound according to claim 15, or mixtures thereof, and a compatible carrier.

36. A method for preventing or destroying plants which comprises applying a herbicidally effective amount of a compound according to claim 1, or mixtures thereof, to the foliage or potential growth medium of said plants.

37. A method for preventing or destroying plants which comprises applying a herbicidally effective amount of a compound according to claim 28, or mixtures thereof, to the foliage or potential growth medium of said plants.

38. A method for preventing or destroying plants which comprises applying a herbicidally effective amount of a compound according to claim 15, or mixtures thereof, to the foliage or potential growth medium of said plants.

39. A plant growth regulating composition which comprises an amount of a compound according to claim 1, or mixtures thereof, effective to alter the growth pattern of plants.

40. A method for regulating the growth of plants which comprises applying to the foliage of said plants or their growth medium an amount of a compound according to claim 1, or mixtures thereof, effective to alter the growth pattern of such plants.

* * * * *